United States Patent [19]
Ostermayer et al.

[11] Patent Number: 4,818,766
[45] Date of Patent: Apr. 4, 1989

[54] NOVEL PHENOXYALIPHATYLPHENYLENEOXY-ALKYL ESTERS AND AMIDES

[75] Inventors: Franz Ostermayer; Markus Zimmermann, both Riehen, Switzerland

[73] Assignee: Ciba-Geigy Corporation, Ardsley, N.Y.

[21] Appl. No.: 75,156

[22] Filed: Jul. 20, 1987

[30] Foreign Application Priority Data

Jul. 22, 1986 [CH] Switzerland .......................... 2918/86

[51] Int. Cl.$^4$ .................. A61K 31/455; C07D 211/90
[52] U.S. Cl. ..................................... 514/356; 514/333; 514/334; 514/338; 514/339; 514/344; 514/349; 514/350; 514/352; 514/355; 546/256; 546/257; 546/291; 546/273; 546/271297; 546/298; 546/286; 546/288; 546/309; 546/310; 546/316; 546/321; 546/322

[58] Field of Search ............... 546/256, 257, 271, 273, 546/291, 297, 298, 286, 288, 289, 309, 310, 316, 321, 322; 514/333, 334, 338, 339, 344, 349, 350, 352, 355, 356

[56] References Cited

FOREIGN PATENT DOCUMENTS

| 151006 | 8/1985 | European Pat. Off. . |
| 179386 | 4/1986 | European Pat. Off. . |
| 191724 | 8/1986 | European Pat. Off. . |
| 194046 | 9/1986 | European Pat. Off. . |
| 194752 | 9/1986 | European Pat. Off. . |
| 218068 | 4/1987 | European Pat. Off. . |
| 2640 | 5/1986 | World Int. Prop. O. .......... 546/321 |

OTHER PUBLICATIONS

WO 86/02640 (5/86).
WO 86/04581 (8/86).
Derwent Abstract of Japanese J6 1143359 (7/86).

Primary Examiner—Jane T. Fan
Attorney, Agent, or Firm—Irving M. Fishman

[57] ABSTRACT

The invention relates to novel 1,4-dihydropyridine-3-carboxylic acid phenoxyaliphatylphenyleneoxyalkyl esters of the formula

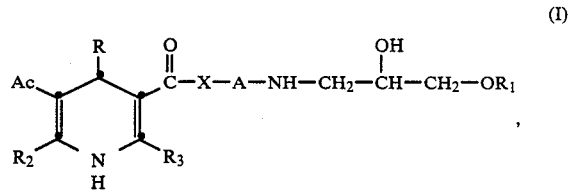

(I)

in which Ac represents an acyl group, X represents oxy or optionally substituted imino, A represents a divalent aliphatic hydrocarbon radical interrupted by a group $-X_1-Ph-X_2-$ in which at least one of the radicals $X_1$ and $X_2$ represents oxy and a radical $X_1$ or $X_2$ that is other than oxy represents a direct bond, and Ph represents an optionally substituted phenylene radical, and R represents an optionally substituted phenyl, pyridyl or 1-oxidopyridyl, (1,3-dioxa)indanyl or benzofurazanyl radical, $R_1$ represents an optionally substituted phenyl or indolyl radical, $R_2$ represents an aliphatic hydrocarbon radical and $R_3$ represents an aliphatic radical, cyano or amino, and acid addition salts thereof.

23 Claims, No Drawings

NOVEL PHENOXYALIPHATYLPHENYLENEOXYALKYL ESTERS AND AMIDES

The invention relates to novel 1,4-dihydro-pyridine-3-carboxylic acid phenoxyaliphatylphenyleneoxyalkyl esters of the formula

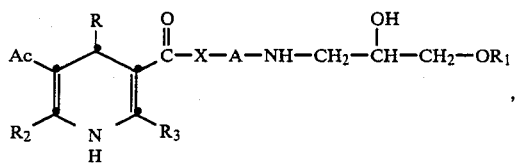

(I)

in which Ac represents an acyl group, x represents oxy or optionally substituted imino, A represents a divalent aliphatic hydrocarbon radical interrupted by a group $-X_1-Ph-X_2-$ in which at least one of the radicals $X_1$ and $X_2$ represents oxy and a radical $X_1$ or $X_2$ that is other than oxy represents a direct bond, and Ph represents an optionally substituted phenylene radical, and R represents an optionally substituted phenyl, pyridyl or 1-oxidopyridyl, (1,3-dioxa)indanyl or benzofurazanyl radical, $R_1$ represents an optionally substituted phenyl or indolyl radical, $R_2$ represents an aliphatic hydrocarbon radical and $R_3$ represents an aliphatic radical, cyano or amino, and acid addition salts thereof.

Acyl groups Ac are derived, for example, from aliphatic carboxyllic or sulphonic acids or from semiesters of carbonic acid and are, for example, lower alkoxycarbonyl, lower alkanesulphonyl or lower alkanoyl.

Substituted imino is, for example, aliphatically substituted and is, for example, lower alkylimino.

Phenylene is 1,2-, 1,3- and especially 1,4-phenylene.

As substituents of aromatic radicals Ph, R and $R_1$ there come into consideration, for example, for Ph: lower alkyl, lower alkoxy, halogen, trifluoromethyl and/or nitro; for R: lower alkyl, lower alkoxy, halo-lower alkoxy, lower alkenyloxy, halogen, trifluoromethyl, cyano, optionally lower alkyl-, lower alkoxy-, halo-, trifluoromethyl- and/or nitro-substituted benzylthio or benzyloxy radicals and/or nitro; and for $R_1$: lower alkyl, lower alkoxy-lower alkyl, lower alkoxy-lower alkoxy-lower alkyl, cycloalkyl-lower alkoxy-lower alkyl, carbamoyl-lower alkyl, lower alkanoylamino-lower alkyl, lower alkoxy, lower alkenyloxy, lower alkynyloxy, lower alkoxy-lower alkoxy-carbamoyl-lower alkoxy, lower alkanoylamino-lower alkoxy, halogen, lower alkanoyl and/or cyano.

Divalent aliphatic hydrocarbon radicals as constituents of A are, for example, alkylene radicals, for example $C_2-C_{14}$-alkylene, especially lower alkylene.

Aliphatic hydrocarbon radicals $R_2$ are, for example, lower alkyl radicals.

Aliphatic radicals $R_3$ are, for example, optionally electro-negatively substituted, such as hydroxylated, lower alkyl radicals, especially lower alkyl and hydroxy-lower alkyl.

Radicals A are, for example, lower alkyleneoxyphenyleneoxy-lower alkylene or lower alkylene- or lower alkylidene-phenyleneoxy-lower alkylene radicals. Radicals $-X-A-$ are accordingly, for example, those of the formula $-X-alk_1-O-Ph-alk_2-$ or $-X-alk_1-O-Ph-O-alk_3-$ in which $alk_1$ and $alk_3$ represent identical or different lower alkylene radicals, $alk_2$ represents lower alkylene or lower alkylidene and X and Ph have the meanings given above.

Phenyl, pyridyl and 1-oxidopyridyl radicals R, phenyl and indolyl radicals $R_1$ and phenylene radicals Ph as constituents of the group A may contain up to and including 3, especially 1 or 2, of the mentioned substituents. Phenyl radicals R, which are optionally substituted as indicated, are unsubstituted or preferably are mono- or di-substituted, preferably in the 2- and/or 3-position(s), for example, by lower alkyl, lower alkoxy, halo-lower alkoxy, lower alkenyloxy, halogen, trifluoromethyl, cyano, benzylthio, benzyloxy or by nitro. Pyridyl and 1-oxidopyridyl radicals R are, for example, 3-(1-oxido)-pyridyl radicals that are unsubstituted or, especially, are monosubstituted, preferably 2-substituted, by lower alkyl, lower alkoxy, optionally S-oxidised lower alkylthio or by halogen. Benzofurazanyl radicals and (1,3-dioxa)indanyl radicals R are preferably unsubstituted and are, for example, 8-benzofurazanyl and 4-(1,3-dioxa)indanyl, respectively. Phenyl radicals $R_1$ are unsubstituted or are monosubstituted, for example, by lower alkyl, lower alkoxy-lower alkyl, lower alkoxy-lower alkoxy-lower alkyl, cycloalkyl-lower alkoxy-lower alkyl, carbamoyl-lower alkyl, lower alkanoylamino-lower alkyl, lower alkoxy, lower alkenyloxy, lower alkynyloxy, lower alkoxy-lower alkoxy, carbamoyl-lower alkoxy, lower alkanoylamino-lower alkoxy or by cyano. Phenylene radicals Ph as constituents of the group A are preferably unsubstituted. Indolyl radicals $R_1$ are indolyl radicals, especially 4-indolyl radicals, that are unsubstituted or, preferably, are monosubstituted, especially 2-substituted, by lower alkyl.

Hereinbefore and hereinafter "lower" organic radicals are to be understood as being, for example, radicals that contain per "lower" partial structure up to and including 7, especially up to and including 4, carbon atoms (C atoms).

Lower alkoxycarbonyl is, for example, $C_1-C_4$-alkoxycarbonyl, such as methoxy-, ethoxy-, propoxy-, isopropoxy-, butoxy-, isobutoxy-, sec.-butoxy- or tert.-butoxy-carbonyl, but may also be $C_5-C_7$-alkoxycarbonyl group, such as pentyloxy-, hexyloxy- or heptyloxycarbonyl group.

Lower alkanesulphonyl is, for example, $C_1-C_4$-alkanesulphonyl, especially methanesulphonyl, also propane-1- or propane-2-sulphonyl, butanesulphonyl or, in the case of a group Ac, 2-methylpropane-2-sulphonyl.

Lower alkanoyl is, for example, $C_1-C_7$-alkanoyl, especially $C_2-C_5$-alkanoyl, such as, especially, acetyl, propionyl, butyryl, isobutyryl, valeroyl, isovaleroyl or pivaloyl, but may also be formyl or a hexanoyl or heptanoyl group.

Lower alkylimino is, for example, $C_1-C_4$-alkylimino, such as methylimino.

Lower alkyl is, for example, $C_1-C_4$-alkyl, such as methyl, ethyl, propyl, isopropyl, butyl, isobutyl, sec.-butyl or tert.-butyl, but may also be a $C_5-C_7$-alkyl group, such as a pentyl, hexyl or heptyl group.

Lower alkoxy is, for example, $C_1-C_4$-alkoxy, such as methoxy, ethoxy, propoxy, isopropoxy or butoxy, and also isobutoxy, sec.-butoxy or tert.-butoxy.

Halogen is especially halogen having an atomic number of up to and including 35, such as fluorine, chlorine or bromine, and also iodine.

Halo-lower alkoxy is, for example, halo-, dihalo-, trihalo- or tetrahalo-$C_1$-$C_4$-alkoxy in which there come into consideration as halo substituent(s) especially identical or different halogen atoms having an atomic number of up to and including 35, such as chlorine or especially fluorine, such as difluoromethoxy or 1,1,2-trifluoro-2-chloroethoxy.

Lower alkenyloxy is, for example, $C_2$-$C_4$-alkenyloxy, such as allyloxy or methallyloxy.

Lower alkoxy-lower alkyl is, for example, $C_1$-$C_4$-alkoxy-$C_1$-$C_4$-alkyl, for example 2-methoxyethyl, 2-ethoxyethyl or 2-isopropoxyethyl. Similarly, lower alkoxy-lower alkoxy is, for example, ω-$C_1$-$C_4$-alkoxy-$C_2$-$C_4$-alkoxy, for example 2-methoxyethoxy, 2-ethoxyethoxy or 2-isopropoxyethoxy.

Lower alkoxy-lower alkoxy-lower alkyl carries the terminal lower alkoxy group in a position higher than the α-position and is, for example, corresponding $C_1$-$C_4$-alkoxy-$C_2$-$C_4$-alkyl, such as 2-methoxyethoxymethyl or 2-isopropoxyethoxymethyl.

Cycloalkyl-lower alkoxy-lower alkyl carries the cycloalkyl-lower alkoxy group in a position higher than the α-position and is, for example, cycloalkyl-$C_1$-$C_4$-alkoxy-$C_1$-$C_4$-alkyl having from 3 up to and including 5 ring members in the cycloalkyl moiety, such as 2-cyclopropylmethoxyethyl.

Carbamoyl-lower alkyl is, for example, carbamoyl-$C_1$-$C_4$-alkyl, such as carbamoylmethyl. Correspondingly, carbamoyl-lower alkoxy is, for example, carbamoyl-$C_1$-$C_4$-alkoxy, such as carbamoylmethoxy.

Lower alkanoylamino-lower alkyl is, for example, $C_2$-$C_7$-alkanoyl-, especially $C_2$-$C_4$-alkanoyl-amino-$C_1$-$C_4$-alkyl, such as acetylaminomethyl or 2-acetylaminoethyl.

Lower alkynyloxy is, for example, $C_2$-$C_4$-alkenyloxy, such as propargyloxy.

Carbamoyl-lower alkyl is, for example, carbamoyl-$C_1$-$C_4$-alkyl, such as carbamoylmethyl. Correspondingly, carbamoyl-lower alkoxy is, for example, carbamoyl-$C_1$-$C_4$-alkoxy, such as carbamoylmethoxy.

Lower alkanoylamino-lower alkoxy is, for example, ω-$C_2$-$C_7$-alkanoyl-, especially $C_2$-$C_4$-alkanoyl-amino-$C_2$-$C_4$-alkoxy, such as 2-acetylaminoethoxy.

Hydroxy-lower alkyl is, for example, hydroxy-$C_1$-$C_4$-alkyl, such as hydroxymethyl or 2-hydroxyethyl.

Lower alkyleneoxyphenyleneoxy-lower alkylene radicals are, for example, $C_2$-$C_4$-alkyleneoxyphenyleneoxy-$C_2$-$C_4$-alkylene radicals having from 10 up to and including 14 members, for example of the formula —alk$_1$—O—Ph—O—alk$_3$— in which alk$_1$ and alk$_3$ represent identical or different $C_2$-$C_4$-alkylene radicals of the kind defined above and Ph represents phenylene, especially p-phenylene, such as ethyleneoxyphenyleneoxyethylene, ethyleneoxyphenyleneoxy-1,2-propylene or ethyleneoxyphenyleneoxy-1,2-(2-methyl)-propylene, and also 1,3-propyleneoxyphenyleneoxyethylene.

Lower alkylenephenyleneoxy-lower alkylene radicals are, for example, $C_1$-$C_4$-alkylenephenyleneoxy-$C_2$-$C_4$-alkylene or $C_2$-$C_4$-alkyleneoxyphenylene-$C_1$-$C_4$-alkylene radicals having from 8 up to and including 14 members, for example of the formula —alk$_1$—O—Ph—alk$_2$— in which alk$_1$ represents $C_2$-$C_4$-alkylene of the kind defined above, alk$_2$ represents $C_2$-$C_4$-alkylene or $C_1$-$C_4$-alkylidene of the kind defined above and Ph represents phenylene, especially p-phenylene, such as ethyleneoxyphenyleneethylene.

Lower alkylidenephenyleneoxy-lower alkylene is, for example, of the formula —alk$_2$—Ph—O—alk$_3$—, such as $C_1$-$C_4$-alkylidenephenyleneoxy-$C_2$-$C_4$-alkylene, for example methylene-, ethylidene- or isopropylidene-1,4-phenyleneoxyethylene.

Lower alkylene is, for example, $C_2$-$C_4$-alkylene of which the free valencies originate from adjacent carbon items or from carbon items in the 1,3- or 1,4-position relative to one another, and represents as alk$_1$, for example, ethylene or, secondly, 1,3-propylene or 1,4-butylene, and as alk$_3$, for example, ethylene, 1,2-propylene or 1,2-(2-methyl)-propylene.

Lower alkylidene alk$_2$ is, for example, $C_1$-$C_4$-alkylidene of which the free valencies originate from the same carbon atom and represents, for example, methylene, ethylidene, propylidene or isopropylidene.

Pyridyl is 2-, 3- or 4-pyridyl and 1-oxidopyridyl is 1-oxido-2-pyridyl, -3-pyridyl or -4-pyridyl, whilst benzofurazanyl (also 2,1,3-benzooxadiazolyl) is especially 4-benzofurazanyl, and indolyl is, for example, 2-, 3- and especially 4-indolyl.

Optionally S-oxidised lower alkylthio is lower alkylthio, lower alkanesulphinyl or lower alkanesulphonyl.

Lower alkylthio is, for example, $C_1$-$C_4$-alkylthio, especially methylthio, also ethylthio, propylthio, isopropylthio or butylthio.

Lower alkanesulphinyl is, for example, $C_1$-$C_4$-alkanesulphinyl, especially methanesulphinyl, also propane-1- or propane-2-sulphinyl or butanesulphinyl.

The compounds of the formula I can be in the form of salts, especially acid addition salts, more especially corresponding pharmaceutically acceptable, non-toxic acid addition salts. Such salts are, for example, those with hydrohalic acids, for example hydrochloric acid or hydrobromic acid, also nitric acid, sulphuric acid or phosphoric acid, or organic acids, such as carboxylic acids, for example acetic acid, propionic acid, glycolic acid, succinic acid, maleic acid, hydroxymaleic acid, methylmaleic acid, fumaric acid, malic acid, tartaric acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and also amino acids, or organic sulphonic acids, such as optionally hydroxy-containing lower alkanesulphonic acids, for example methanesulphonic acid, ethanesulphonic acid, 2-hydroxyethanesulphonic acid or ethane-1,2-disulphonic acid, or arylsulphonic acid, for example benzenesulphonic acid, 4-methylbenzenesulphonic acid or naphthalene-2-sulphonic acid, or with other acidic organic substances, such as ascorbic acid. Corresponding acid addition salts are preferably formed with the basic centre of the side chain. Also included are salts that are unsuitable for pharmaceutical uses, since they can be used, for example, for the isolation and purification of free compounds according to the invention or of other pharmaceutically acceptable salts.

The compounds of the formula I and their salts have valuable pharmacological properties, especially in the cardiovascular field. They act as calciumantagonists and at the same time as β-receptor blockers.

They have a marked ability to bond to calcium channels. This property can be demonstrated in vitro at concentrations of about 1 to about 8 nmols/l as displacement of $^3$H—ni—trendipine from its bonding sites to the myocardial membranes of guinea pigs analogously to the method of Erne, P. et al., Biochem. Biophys. Res. Com. 118, 842 (1984).

Furthermore, the compounds of the formula I at the same time exhibit β-receptor binding effects. These properties can be demonstrated in vitro at concentrations of about 2 to about 250 nmols/1 as displacement of $^3$H-dihydroalprenolol from its bonding sites to the cerebral membranes of rats, analogously to the method of Bylund and Snyder, Mol. Pharmacol. 12, 568 (1976). It should be noted, especially, that, if the affinity to the β$_1$- and β$_2$-receptors is measured in the same test procedure separately, several of the compounds exhibit a significant β$_1$-selectivity (β$_2$/β$_1$ ratio: about 30 to about 100).

In a further pharmacological test model, in which the influence of the compounds on pressor and trachycardial effects, induced by various agonists (for example, angiotensine II, noradrenalin, adrenalin) or by electrical stimulation of the sympathetic nervous system in spinalised rats, can be investigated, it has been observed, for example in a dosage range of from approximately 10 to approximately 30 mg/kg p.o., that the compounds of the formula I on the one hand inhibit a rise in blood pressure (as an expression of the calcium antagonistic activity) and, on the other hand, inhibit an increase in heart rate (as an expression of the β-receptor blocking effect) to a similar extent. Accordingly, the compounds of the formula I and their pharmaceutically acceptable salts can be used, for example, as pharmaceuticals, in general those conditions, where calcium-antagonists and β-receptor blockers are known to be indicated, in particular in the treatment of hypertension and Angina pectoris. The invention relates also to the use of the compounds according to the invention for the manufacture of medicaments, especially antihypertensives, antianginals and anti-arrhythmics, for the therapeutic and prophylactic treatment of the human and animal body. The commercial formulation of the active ingredients may also be included.

The invention relates especially to compounds of the formula I in which Ac represents lower alkoxycarbonyl, lower alkanoyl or lower alkanesulphonyl, X represents oxy, imino or lower alkylimino, A represents an alkylene radical interrupted by a group of the formula —X$_1$—Ph—X$_2$ in which at least one of the radicals X$_1$ and X$_2$ represents oxy and a radical X$_1$ or X$_2$ that is other than oxy represents a direct bond, and Ph represents a phenylene radical that is unsubstituted or is substituted by lower alkyl, lower alkoxy, halogen, trifluoromethyl and/or by nitro, and R represents a phenyl radical optionally substituted by lower alkyl, by lower alkoxy, by halo-lower alkoxy, by lower alkenyloxy, by halogen, by trifluoromethyl, by cyano, by an optionally lower alkyl-, lower alkoxy-, halo-, trifluoromethyl- and/or nitro-substituted benzylthio or benzyloxy radical and/or by nitro, or represents an optionally 1-oxidised pyridyl radical optionally substituted by lower alkyl, lower alkoxy, optionally S-oxidised lower alkylthio and/or by halogen, or represents a (1,3-dioxa)indanyl or benzofurazanyl radical, R$_1$ represents a phenyl radical optionally substituted by lower alkyl, lower alkoxy-lower alkyl, lower alkoxy-lower alkoxy-lower alkyl, cycloalkyl-lower alkoxy-lower alkyl, carbamoyl-lower alkyl, lower alkanoylamino-lower alkyl, lower alkoxy, lower alkenyloxy, lower alkynyloxy, lower alkoxy-lower alkoxy, carbamoyl-lower alkoxy, lower alkanoylamino-lower alkoxy and/or by cyano, or represents an indolyl radical optionally substituted by lowerr alkyl, R$_2$ represents lower alkyl and R$_3$ represents lower alkyl, hydroxy-lower alkyl, cyano or amino, and acid addition salts thereof.

The invention relates especially to compounds of the formula I in which Ac represents $C_1$-$C_7$-alkanoyl, $C_1$-$C_7$-alkoxycarbonyl or $C_1$-$C_4$-alkanesulphonyl, X represents oxy, imino or $C_1$-$C_4$-alkylimino, A represents a $C_1$-$C_4$-alkylenephenyleneoxy-$C_2$-$C_4$-alkylene or $C_2$-$C_4$-alkyleneoxyphenylene-$C_1$-$C_4$-alkylene radical having from 8 up to and including 14 members or a $C_1$-$C_4$-alkyleneoxyphenyleneoxy-$C_1$-$C_4$-alkylene radical having from 10 up to and including 14 members, each optionally substituted in the phenylene moiety by $C_1$-$C_4$-alkyl, $C_1$-$C_4$-alkoxy, halogen, trifluoromethyl and/or by nitro, R represents a phenyl radical optionally substituted by $C_1$-$C_4$-alkyl, by $C_1$-$C_4$-alkoxy, by mono- up to and including tetra-halo-$C_1$-$C_4$-alkoxy, $C_2$-$C_4$-alkenyloxy, by an optionally $C_1$-$C_4$-alkyl-, $C_1$-$C_4$-alkoxy-, halo-, trifluoromethyl- and/or nitro-substituted benzylthio or benzyloxy radical, by halogen, by trifluoromethyl, by cyano and/or by nitro, or represents a pyridyl or 1-oxidopyridyl radical, preferably a 3-pyridyl or 3-(1-oxido)-pyridyl radical, optionally substituted by $C_1$-$C_4$-alkyl, $C_1$-$C_4$-alkoxy, $C_1$-$C_4$-alkylthio, $C_1$-$C_4$-alkanesulphinyl, $C_1$-$C_4$-alkanesulphonyl and/or by halogen, or represents a 4-(1,3-dioxa)indanyl or 8-benzofurazanyl radical, R$_1$ represents a phenyl radical optionally substituted by $C_1$-$C_4$-alkyl, $C_1$-$C_4$-alkoxy-$C_2$-$C_4$-alkyl, $C_1$-$C_4$-alkoxy-$C_2$-$C_4$-alkoxy-$C_1$-$C_4$-alkyl, 3- to 5-membered cycloalkyl-$C_1$-$C_4$-alkoxy-$C_2$-$C_4$-alkyl, carbamoyl-$C_1$-$C_4$-alkyl, $C_2$-$C_7$-alkanoylamino-$C_1$-$C_4$-alkyl, $C_1$-$C_4$-alkoxy, $C_2$-$C_4$-alkenyloxy, $C_2$-$C_4$-alkynyloxy, ω-$C_1$-$C_4$-alkoxy-$C_2$-$C_4$-alkoxy, carbamoyl-$C_1$-$C_4$-alkoxy, ω-$C_2$-$C_7$-alkanoylamino-$C_2$-$C_4$-alkoxy and/or by cyano, or represents an indolyl radical optionally substituted by $C_1$-$C_4$-alkyl, R$_2$ represents $C_1$-$C_4$-alkyl and R$_3$ represents $C_1$-$C_4$-alkyl, hydroxy-$C_1$-$C_4$-alkyl, cyano or amino, and acid addition salts thereof.

The invention relates more especially to compounds of the formula I in which Ac represents $C_1$-$C_4$-alkoxycarbonyl, such as methoxycarbonyl, X represents oxy, —X—A— represents a radical of the formula —X—alk$_1$—O—Ph—alk$_2$— or —X—alk$_1$—O—Ph—O—alk$_3$— in which alk$_1$ and alk$_2$ represent identical or different $C_2$-$C_4$-alkylene radicals, alk$_1$ representing, for example, ethylene and alk$_3$ representing, for example, ethylene, 1,2-propylene or 1,2-(2-methyl)-propylene, and alk$_2$ representing $C_2$-$C_4$-alkylene, for example ethylene or 1,3-propylene, or $C_1$-$C_4$-alkylidene, for example methylene or ethylidene, such as 2-(p-ethylenephenoxy)-ethoxy, 2-(p-ethyleneoxyphenoxy)-ethoxy, 2-(p-ethylenephenoxy)-ethylene, 2-[p-(2-propyleneoxy)-phenoxy]-ethoxy or 2-{p-[2-(2-methylpropyleneoxy)]-phenoxy}-ethoxy, and R represents phenyl that is unsubstituted or is mono- or di-substituted, preferably in the 2- and/or 3-position(s), by halogen having an atomic number of up to and including 35, such as chlorine, or is monosubstituted by trifluoromethyl, nitro or by cyano, R$_1$ represents phenyl optionally monosubstituted by $C_1$-$C_4$-alkoxy-$C_2$-$C_4$-alkoxy, such as 2-methoxyethoxy, $C_1$-$C_4$-alkoxy-$C_1$-$C_4$-alkyl, such as 2-methoxyethyl, $C_1$-$C_4$-alkoxy-$C_2$-$C_4$-alkoxy-$C_1$-$C_4$-alkyl, such as 2-isopropoxyethoxymethyl, 3- to 5-membered cycloalkyl-$C_1$-$C_4$-alkoxy-$C_2$-$C_4$-alkyl, such as 2-cyclopropylmethoxyethyl, carbamoyl-$C_1$-$C_4$-alkyl, such as carbamoylmethyl, or by cyano, and R$_2$ and R$_3$ represent $C_1$-$C_4$-alkyl, such as methyl, and acid addition salts thereof.

The invention relates more especially to compounds of the formula I in which R$_1$ represents phenyl, 2-methyl-, 4-(2-methoxyethyl)-, 4-(2-isopropoxyethoxymethyl)-, 4-(2-methoxyethoxy)-4-(2-isopropoxyethoxy)-, 4-(2-cyclopropylmethoxyethyl)-, 4-carbamoylmethyl-, 2-methoxy-, 2-isopropoxy- or 2-cyano-phenyl, 4-indolyl or 2-methyl-4-indolyl.

The invention relates more especially to compounds of the formula I in which Ac represents $C_1-C_4$-alkoxycarbonyl, such as methoxycarbonyl, —X—A— represents a group of the formula —X—$alk_1$—O—Ph—$alk_3$— or X—$alk_1$—O—Ph—O—$alk_3$ in which X represents oxy, each of $alk_1$ and $alk_3$, independently of the other, represents $C_2-C_4$-alkylene, such as ethylene, 1,2- or 1,3-propylene or 1,2-(2-methyl)-propylene, and Ph represents 1,2-, 1,3- or 1,4-phenylene, and R represents phenyl that is mono- or di-substituted in the 2- and/or 3-position(s) by halogen having an atomic number of up to and including 35, such as chlorine, or is monosubstituted by $C_1-C_4$-alkoxy, such as methoxy, especially in the 3-position, or by nitro, especially in the 2- or 3-position, $R_1$ represents phenyl monosubstituted by 2-methoxyethyl, 2-isopropoxyethoxymethyl, 2-cyclopropylmethoxyethyl, 2-methoxyethoxy or by 2-isopropoxyethoxy, in each case especially in the 4-position, or monosubstituted by cyano, especially in the 2-position, and each of $R_2$ and $R_3$ represents $C_1-C_4$-alkyl, such as methyl, and acid addition salts thereof.

The invention relates more especially to compounds of the formula I in which Ac represents $C_1-C_4$-alkoxycarbonyl, such as methoxycarbonyl, —X—A— represents a group of the formula —X—$alk_1$—O—Ph—$alk_3$— or —X—$alk_1$—O—Ph—O—$alk_3$ in which X represents oxy, each of $alk_1$ and $alk_3$, independently of the other, represents $C_2-C_4$-alkylene, such as ethylene, 1,2- or 1,3-propylene or 1,2-(2-methyl)-propylene, and Ph represents 1,4-phenylene, and also 1,2- and 1,3-phenylene, and R represents 3-nitro- or 3-methoxy-phenyl, $R_1$ represents 4-(2-methoxyethyl)-, 4-(2-isopropoxyethoxymethyl)-, 4-(2-cyclopropylmethoxyethyl)-, 4-(2-methoxyethoxy)-4-(2-isopropoxyethoxy)-phenyl or 2-cyanophenyl, and each of $R_2$ and $R_3$ represents $C_1-C_4$-alkyl, such as methyl, and acid addition salts thereof.

The invention relates more especially to compounds of the formula I in which Ac represents $C_1-C_3$-alkoxycarbonyl, such as methoxycarbonyl, —X—A— represents a group of the formula —X—$C_2H_4$—O—Ph—$alk_3$— or —X—$C_2H_4$—O—Ph—O—$alk_3$— in which X represents oxy, Ph represents 1,4- or 1,2-phenylene, and $alk_3$ represents $C_2-C_4$-alkylene, such as ethylene or 1,2-(2-methyl)-propylene, and R represents 3-nitro- or 3-methoxy-phenyl, $R_2$ and $R_3$ represent $C_1-C_2$-alkyl, such as methyl, and $R_1$ represents 4-(2-methoxyethyl)-, 4-(1-isopropoxyethoxymethyl)-, 4-(2-cyclopropylmethoxyethyl)- or 4-(2-methoxyethoxy)-phenyl, or $R_1$ represents 2-cyanophenyl, and acid addition salts thereof.

The invention relates more specifically to compounds of the formula I in which Ac represents $C_1-C_3$-alkoxycarbonyl, such as methoxycarbonyl, —X—A— represents a group of the formula —X—$C_2H_5$—O—Ph—O—$alk_3$ in which X represents oxy, Ph represents 1,4-phenylene, and $alk_3$ represents ethylene or 1,2-(2-methyl)-propylene, and R represents 3-nitrophenyl, $R_1$ represents 4-(2-methoxyethyl)- or 4-(2-isopropoxyethoxymethyl)-phenyl, and $R_2$ and $R_3$ represent $C_1-C_2$-alkyl, such as methyl, and acid addition salts thereof.

The pharmacological properties are especially favourable when the asymmetric carbon atom of the group —NH—$CH_2$—CHOH—$CH_2$—$OR_1$ is in the S-configuration in accordance with the rule of Cahn, Ingold and Prelog:

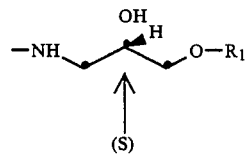

The invention relates specifically to the compounds of the formula I mentioned in the Examples and to their acid addition salts and to processes for their manufacture.

The invention relates also to a process for the manufacture of compounds of the formula I and their acid addition salts, which process is based on methods known per se. The process according to the invention is characterised in that (a) a compound of the formula

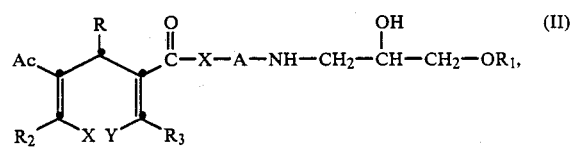

in which one of the radicals X and Y represents a group of the formula —$NH_2$ and the other represents hydroxy or a group of the formula —$NH_2$, or a tautomer thereof or a corresponding tautomeric mixture, is cyclised, or (b) a compound of the formula R-CHO (III), or a reactive functional derivative thereof, is reacted with a compound of the formula

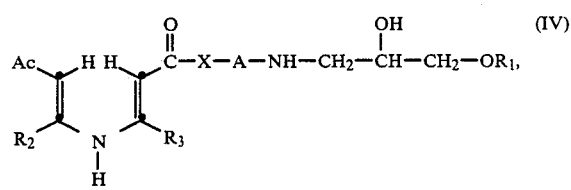

or with a tautomer thereof or with a corresponding tautomeric mixture, or (c) in a compound of the formula

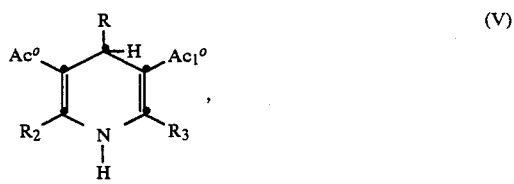

in which Ac° represents a group —Ac or a radical that can be converted into a group —Ac and $Ac_1$° represents a radical that can be converted into a group of the formula

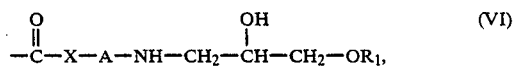

or Ac° represents a radical that can be converted into a group Ac and $Ac_1$° represents a group of the formula VI, Ac° is converted into a group Ac and/or Ac₁° is converted into a group of the formula VI, or (d) a compound of the formula

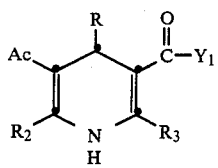
(VII)

is reacted with a compound of the formula

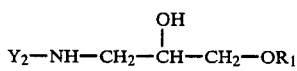
(VIII)

in which Y₁ represents a group Y and Y₂ represents a group of the formula H—X—A—, or Y₁ represents a group of the formula —X—A—Y and Y₂ represents hydrogen, or Y₁ represents a group of the formula —X—H and Y₂ represents a group of the formula Y—A—, and Y represents a removable radical in each case, or (e) a compound of the formula

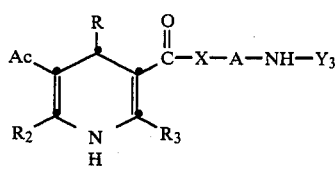
(IX)

is reacted with a compound of the formula

  Y₄—OR₁ (X)

in which one of the radicals Y₃ and Y₄ represents hydrogen and the other represents a group of the formula

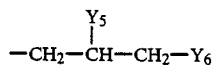
(XI)

in which Y₅ represents hydroxy and Y₆ represents a removable radical, or Y₅ and Y₆ together represent an epoxy group, and, if desired, a resulting compound of the formula I is converted into a different compound of the formula I and/or a resulting free compound of the formula I is converted into a salt, or a resulting salt is converted into the free compound or into a different salt, and/or, if desired, a resulting mixture of isomers is separated into the individual isomers.

Customarily, the starting materials of the formula II used in process variant (a) are formed in situ, so that the ring closure according to the process takes place under the reaction conditions for the manufacture of the starting material. For example, the starting materials of the formula II and, under the reaction conditions, customarily also the corresponding end products of the formula I, can be obtained by (aa) reacting a compound of the formula R-CHO (III), or a reactive functional derivative thereof, with a compound of the formula

(IIa)

and with a compound of the formula

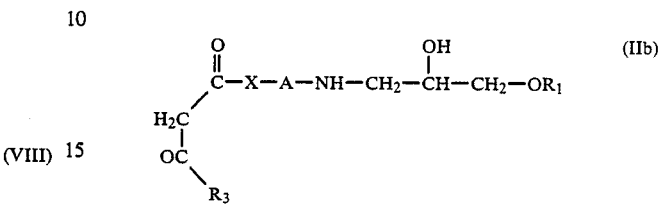
(IIb)

and with ammonia, or (ab) reacting a compound of the formula III, or a reactive functional derivative thereof, with a compound of the formula

(IIc)

and with a compound of the formula IIb, or (ac) reacting a compound of the formula III, or a reactive functional derivative thereof, with a compound of the formula

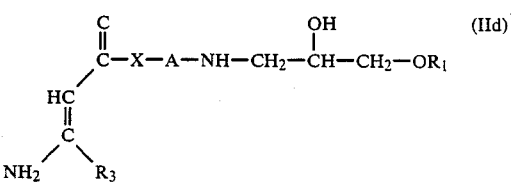
(IId)

and with a compound of the formula IIa or IIc, or (ad) reacting ammonia with a compound of the formula

(IIe)

and with a compound of the formula IIb, or (ae) reacting ammonia with a compound of the formula

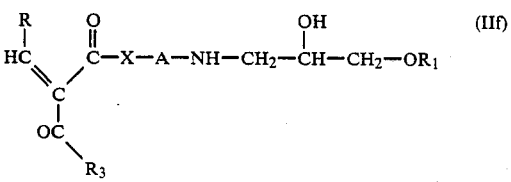
(IIf)

and with a compound of the formula IIa or IIc, or (af) reacting ammonia with a compound of the formula

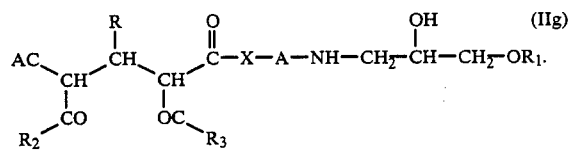

With the exception of the compound of the formula III, the compounds of the formulae IIa to IIg may be used in the form of tautomers or in the form or tautomeric mixtures. Starting materials of the above formulae having salt-forming properties may also be used in the form of salts. Also, in the above compounds the groups R, $R_1$, $R_2$, $R_3$, X, Ac and A have the meanings given in connection with formula I.

Reactive functional derivatives of the aldehyde of the formula III are, inter alia, the corresponding acetals, that is to say the etherified dihydroxymethyl compounds corresponding to the group R, such as dilower alkyl acetals, for example dimethyl or diethyl acetals, acylals, for example the corresponding diacyloxymethyl or dihalomethyl compounds, such as dilower alkanoyl acylals, for example diacetyl acylals, or the corresponding dihalo compounds, for example dichloro or dibromo compounds, and also addition compounds, such as those with an alkali metal hydrogen sulphite, for example potassium hydrogen sulphite.

The ammonia used for the ring closure reactions described hereinbefore may also be used in the form of an agent that yields this compound in situ, for example in the form of an ammonium salt, such as ammonium acetate or ammonium hydrogen carbonate.

The ring closure reaction (a), and the condensation reactions (aa) to (af) for the manufacture of the starting material for the ring closure reaction, customarily formed in situ, are variants of the dihydropyridine synthesis according to Hantzsch. In variant (aa), a total of three molecules of water are removed; in other variants, an addition reaction takes the place of some of the water removal, that is to say the removal of the elements of water occurs as early as during the manufacture of one or two intermediates. In the reaction of compounds of the formula III with compounds of the formulae IId and IIc according to stage (ac), ammonia is removed in addition to or instead of the elements of water. If, in accordance with variant (aa), compounds of the formula I are to be manufactured in which $R_2$ and $R_3$ are different from one another, by-products may be formed that contain the same substituents in the 2- and 6-positions. By not adding all the reactants at the same time, the formation of such by-products can largely be avoided by promoting a certain course of reaction which proceeds in situ according to another variant, since according to the order in which the reactants are added, for example, first of all a compound of the general formula IIc or of the formula IId may be formed.

The ring closure and condensation reactions according to the process are carried out in a manner known per se, if necessary in the presence of a condensation agent, especially a basic condensation agent, such as an excess of a basic reactant or of an additional, for example an organic, base, such as piperidine or ethyldiisopropylamine, or a metal alcoholate, such as an alkali metal lower alkoxide, and/or a suitable dehydrating or water-absorbing agent, also customarily in the presence of an inert organic solvent and at reaction temperatures, for example, in the range of from approximately room temperature to approximately 150° C., especially at the boiling temperature of the solvent. If required, the reaction is carried out in an inert gas atmosphere, for example a nitrogen atmosphere, and/or, for example when using a low-boiling solvent and/or ammonia, in a closed vessel under elevated pressure.

The starting materials used in the process variants are known or can be manufactured according to processes known per se.

For example, starting materials of the formula IIb can be manufactured in customary manner by reacting diketene or compounds of the formula

with compounds of the formula

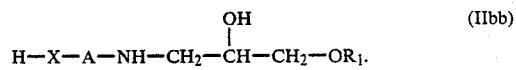

Instead of carboxylic acids of the formula IIba it is also possible to use functional derivatives thereof, such as corresponding carboxylic acid anhydrides, especially mixed anhydrides, such as those with lower alkanecarboxylic acids, for example formic acid, and also acid halides, for example corresponding chlorides or bromides, acid azides, and, further, activated esters, for example cyanomethyl esters. These may be used, optionally in the presence of condensation agents, to form compounds of the formula IIb by reaction with a compound of the formula IIbb, and in the case of free carboxylic acids of the formula IIba also by reaction with compounds of the formula IIbb in which the azido group replaces the group HX—. Carboxylic acids of the formula IIba may also be reacted in the form of salts, especially alkali metal salts or alkaline earth metal salts, with reactive esters of alcohols of the formula IIbb in which X represents oxygen, such as corresponding halides, for example chlorides, bromides or iodides, or organic sulphonic acid esters, for example lower alkanesulphonic acid esters or arenesulphonic acid esters, such as methanesulphonic acid esters or p-toluenesulphonic acid esters, to form corresponding carboxylic acid esters, or corresponding hydrolysable imino esters, such as corresponding imino-lower alkyl esters, are hydrolysed to form the esters. Imino esters of this kind can be obtained in customary manner, for example from nitriles of the formula

corresponding to the compounds of the formula IIba, by reaction with compounds of the formula IIbb in which X represents oxygen, in the presence of an acidic condensation agent, for example hydrogen chloride, in a suitable solvent, for example a solvent of inert character, such as an aromatic substance, for example benzene.

Compounds of the formula IIbb can in turn be obtained in a manner known per se, for example by reacting compounds of the formula $$H-X-A-Y \quad \text{(IIbd)},$$

in which y represents a suitable leaving group, for example a reactive esterified hydroxy group, such as, for example, halogen, for example chlorine, bromine or iodine, or a sulphonyloxy group, for example an arylsulphonyloxy group, such as a p-toluenesulphonyloxy group, with compounds of the formula $$\underset{H_2N-CH_2-CH-CH_2-OR_1,}{\overset{OH}{|}} \quad \text{(IIbe)}$$

advantageously in the presence of a basic condensation agent, such as an oxide, hydroxide or carbonate of an alkali metal or alkaline earth metal, such as sodium hydroxide or calcium carbonate, customarily in the presence of a solvent, for example a lower alkanol, such as ethanol, and at elevated or reduced temperature. Compounds of the formula IIbb can also be used in the form of their metal derivatives in which the hydrogen atom positioned at the nitrogen atom has been replaced by a suitable metal, for example lithium or potassium. In such cases, the described reaction with compounds of the formula IIbd is carried out in an inert anhydrous solvent, for example one of ethereal character, such as tetrahydrofuran, or an aromatic solvent, for example toluene.

Metal compounds corresponding to the formula IIbe can be obtained in customary manner, for example by reaction with a suitable alkali metal-organic compound, for example butyllithium, in an anhydrous solvent, such as tetrahydrofuran, advantageously under a protective gas, for example argon, it being possible for the metal compound present in the reaction mixture to be used for the reaction described above without being isolated.

Compounds of the formula IIbe can, in turn, be manufactured in a manner known per se, for example by reaction of epichlorohydrin first with a compound of the formula $R_1-OH$ (IIbf) and then with ammonia.

The reaction of free carboxylic acids of the formula IIba with compounds of the formula IIbb is advantageously carried out in the presence of an acidic catalyst that promotes removal of the elements of water, such as a protonic acid, for example hydrochloric, hydrobromic, sulphuric, phosphoric or boric acid, benzenesulphonic or toluenesulphonic acid, or a Lewis acid, for example boron trifluoride etherate, in an excess of the alcohol used and/or in an inert solvent, if necessary while removing the water freed during the reaction by distillation, for example azeotropic distillation. Furthermore, the reactions can also be carried out in the presence of waterbinding condensation agents, such as suitably substituted carbodiimides, for example N,N'-diethyl-, N,N'-dicyclohexyl- or N-ethyl-N'-(3-dimethylaminopropyl)-carbodiimide, in inert organic solvents. Mixed anhydrides, especially acid halides, are reacted with alcohols or with alcoholates, for example alkali metal lower alkoxides, for example in the presence of acidbinding agents, for example organic, especially tertiary nitrogen, bases, such as triethylamine, ethyldiisopropylamine or pyridine, or alternatively inorganic bases, for example alkali metal or alkaline earth metal hydroxides or carbonates, such as sodium, potassium or calcium hydroxide or carbonate.

The reactions of activated esters, for example cyanomethyl or pentachlorophenyl esters, with compounds of the formula IIbb are carried out, for example, in a solvent inert towards the reactants in a temperature range of from approximately 0° to approximately 120° C., preferably at from room temperature to approximately 60° C.

The hydrolysis of imido ester starting materials is carried out, for example, by means of watercontaining mineral acids, such as hydrochloric acid or sulphuric acid, it being possible, for example, for the imino ester salts, for example hydrochlorides, obtained during the addition of hydrogen chloride to nitriles and the reaction with anhydrous alcohols, especially unsubstituted or substituted lower alkanols, to be hydrolysed directly to the corresponding esters after the addition of water. It is also possible, for example, to obtain the desired ester compound of the formula IIb from a mixture of nitrile, alcohol and sulphuric acid with a suitable water content without isolation of the imido ester formed in situ.

Starting materials of the formulae IId, IIf and IIg can be manufactured in analogous and customary manner using corresponding starting materials.

In process variant (b), starting materials of the formula IV are formed in situ in a manner analogous to that described for the manufacture of starting materials of the formula II, and the ring closure according to the process to form the end products of the formula I can be carried out under the conditions given for the manufacture of the starting material in the same reaction mixture. Accordingly, starting materials of the formula IV can be obtained by reacting compounds of the formula IIb with those of the formula IIa and ammonia, or by reacting compounds of the formula IIb with those of the formula IIc, or by reacting compounds of the formula IId with those of the formual IIa or IIc, such reactions customarily being carried out in a suitable solvent, for example a lower alkanol, such as ethanol, optionally at elevated or reduced temperature, and advantageously under a protective gas, such as nitrogen.

Starting materials of the formula V for process variant (c) are, for example, those in which Ac° represents carboxy, anhydridised carboxy, such as halocarbonyl, for example chlorocarbonyl, or azidocarbonyl, and Ac₁° represents a group of the formula VI, or in which Ac° represents a radical Ac and Ac₁° represents a group of the formula $$\underset{-C-X-A-N-CH_2-CH-CH_2-OR_1}{\overset{O \qquad\quad Y_7 \quad Y_8-O}{\| \qquad\quad | \qquad |}} \quad \text{(VI')}$$

in which one of the radicals $Y_7$ and $Y_8$ represents hydrogen and the other represents a monovalent substituent that is removable, that is to say replaceable by hydrogen, or $Y_7$ and $Y_8$ together represent a divalent substituent that is removable, that is to say replaceable by hydrogen.

The mentioned groups Ac° may be converted into groups Ac, optionally in the presence of condensation agents, by reaction with a corresponding lower alkanol or with a reactive derivative thereof, for example a corresponding alcoholate, and in the case of free carboxylic acids also by reaction with diazo-lower alkanes.

The conversion of groups $Ac_1°$ of the formula VI' is effected, for example, by removal of the radical(s) $Y_7$ or $Y_8$ or $Y_7+Y_8$, that is to say by replacement thereof by hydrogen.

The removal of the group(s) $Y_7$ or $Y_8$ or $Y_7+Y_8$ is carried out by means of solvolysis, such as hydrolysis, alcoholysis or acidolysis, or by means of reduction including hydrogenolysis.

As removable group $Y_7$ or $Y_8$ there is especially suitable an α-aryl-lower alkyl group that can be removed by hydrogenolysis, such as an optionally substituted 1-polyphenyl-lower alkyl or 1-phenyl-lower alkyl group, for example benzhydryl or trityl, in which substituents, especially of the phenyl moiety, may be, for example, lower alkyl, such as methyl, or lower alkoxy, such as methoxy, benzyl being especially preferred.

The group $Y_7$ or $Y_8$ can also be a radical that can be removed by solvolysis, such as hydrolysis or acidolysis, or by reduction, including hydrogenolysis, especially a corresponding acyl radical, such as the acyl radical of an organic carboxylic acid, for example lower alkanoyl, such as acetyl, or aroyl, such as benzoyl, or the acyl radical of a semi-ester of carbonic acid, such as lower alkoxycarbonyl, for example methoxycarbonyl, ethoxycarbonyl or tert.-butoxycarbonyl, 2-halo-lower alkoxycarbonyl, for example 2,2,2-trichloroethoxycarbonyl or 2-iodoethoxycarbonyl, optionally substituted 1-phenyl-lower alkoxycarbonyl, for example benzyloxycarbonyl or diphenylmethoxycarbonyl, or aroylmethoxycarbonyl, for example phenacyloxycarbonyl, or an optionally substituted 1-polyphenyl-lower alkyl group, for example as indicated above, and more especially trityl.

A removable radical $Y_7+Y_8$, formed by $Y_7$ and $Y_8$ together, is especially a group that can be removed by hydrogenolysis, such as optionally substituted 1-phenyl-lower alkylidene, in which substituents, especially of the phenyl moiety, may be, for example, lower alkyl or lower alkoxy, and is especially benzylidene, or cycloalkylidene, for example cyclopentylidene or cyclohexylidene, or the carbonyl group.

Radicals $Y_7$ and $Y_8$ that can be removed by hydrogenolysis, especially optionally substituted 1-phenyl-lower alkyl groups, more especially benzyl, and also suitable acyl groups, such as optionally substituted 1-phenyl-lower alkoxycarbonyl, and optionally substituted 1-phenyl-lower alkylidene groups formed by the groups $Y_7$ and $Y_8$ together, can be removed by treatment with catalytically activated hydrogen, for example with hydrogen in the presence of a catalyst, such as a suitable noble metal catalyst, for example palladium or platinum.

Groups $Y_8$ that can be removed by hydrolysis, such as acyl radicals of organic carboxylic acids, for example lower alkanoyl, and of semi-esters of carbonic acid, for example lower alkoxycarbonyl, and also, for example, trityl radicals, and lower alkylidene, 1-phenyl-lower alkylidene or cycloalkylidene groups formed by the radicals $Y_7$ and $Y_8$ together, and carbonyl $Y_7+Y_8$, can be removed, depending upon the nature of such radicals, by treatment with water under acidic or basic conditions, for example in the presence of a mineral acid, such as hydrochloric or sulphuric acid, or an alkali metal or alkaline earth metal hydroxide or carbonate, or an amine, such as isopropylamine.

Radicals $Y_8$ that can be removed by acidolysis are especially certain acyl radicals of semi-esters of carbonic acid, such as, for example, tert.-lower alkoxycarbonyl or optionally substituted diphenylmethoxycarbonyl radicals, or a tert.-lower alkyl radical; such radicals can be removed, for example, by treatment with suitable strong organic carboxylic acids, such as lower alkanecarboxylic acids optionally substituted by halogen, especially fluorine, more especially with trifluoroacetic acid (if necessary in the presence of an activating agent, such as anisole), and with formic acid.

Radicals $Y_8$ that can be removed by reduction are to be understood as being also those groups which are removed by treatment with a chemical reducing agent (especially with a reducing metal or a reducing metal compound). Such radicals are especially 2-halo-lower alkoxycarbonyl or arylmethoxycarbonyl which can be removed, for example, by treatment with a reducing heavy metal, such as zinc, or with a reducing heavy metal salt, such as chromium(II) salt, for example the chloride or acetate, customarily in the presence of an organic carboxylic acid, such as formic acid or acetic acid, and water.

The above reactions are customarily carried out in the presence of a solvent or solvent mixture, it being possible for suitable reactants to function simultaneously as solvent, and, if desired, while cooling or heating, for example in an open or closed vessel and/or in the atmosphere of an inert gas, for example nitrogen.

Starting materials that can be used in the form of salts are used especially in the form of acid addition salts, for example with mineral acids and with organic acids.

Those compounds of the formula V in which $Ac°$ represents Ac and $Ac_1°$ represents a group of the formula

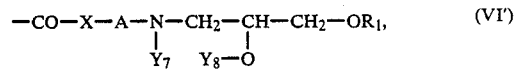

in which $Y_7$ represents a substituent that can be replaced by H, especially 1-phenyl-lower alkyl, more especially benzyl, and $Y_8$ represents hydrogen, are preferred. Advantageously, such a substituent $Y_7$ is replaced by hydrogen by hydrogenolysis.

The starting materials of the formula VI are obtained, for example, by (ca) cyclising a compound of the formula

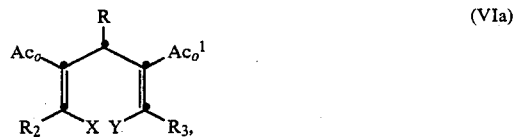

in which one of the radicals X and Y represents a group of the formula $-NH_2$ and the other represents hydroxy or a group of the formula $-NH_2$, or a tautomer thereof or a corresponding tautomeric mixture, or (cb) reacting a compound of the formula R—CHO (III), or a reactive functional derivative thereof, with a compound of the formula

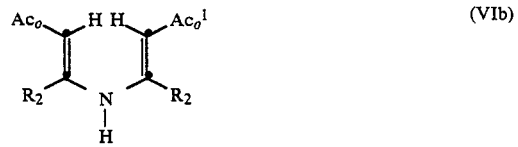

or a tautomer thereof, or (cc) reacting a compound of the formula

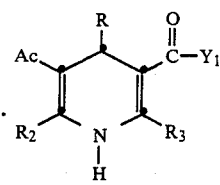

with a compound of the formula

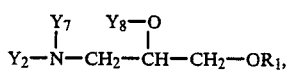

in which $Y_1$ represents a group Y and $Y_2$ represents a group of the formula H—X—A—, or $Y_1$ represents a group of the formula —X—A—Y and $Y_2$ represents hydrogen, or $Y_1$ represents a group of the formula —X—H and $Y_2$ represents a group of the formula Y—A—, and Y represents a removable radical in each case, or (cd) reacting a compound of the formula

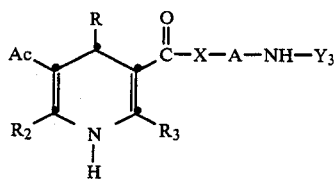

with a compound of the formula

 (X), in which one of the radicals $Y_3$ and $Y_4$ represents hydrogen and the other represents a group of the formula

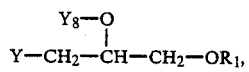

in which Y represents a removable radical. These operations are carried out, for example, in the manner indicated for process variants (a), (b), (d) and (e), respectively.

Removable radicals Y in accordance with process variant (d) are, for example, halogen atoms, such as chlorine, bromine or iodine, and in compounds VII in which $Y_1$ represents a removable radical Y, they may also be optionally etherified hydroxy or, for the reaction with compound VII in which $Y_2$ represents a group H—X—A— and X represents imino, they may be amino groups, and in compounds VII in which $Y_1$ represents a group —X—A—Y or in compounds VII in which $Y_2$ represents a group —A—Y, they may also be hydroxy esterified by a sulphonic acid. Etherified hydroxy is, for example, lower alkoxy, for example methoxy, but may also be optionally substituted phenoxy, for example phenoxy, p-nitrophenoxy or 2,4-dinitrophenoxy. Hydroxy esterified by a sulphonic acid is, for example, lower alkanesulphonyloxy, for example methanesulphonyloxy, or optionally substituted benzenesulphonyloxy, for example benzene-, p-toluene- or p-bromobenzenesulphonyloxy.

The reaction of compounds VII and VIII in accordance with process variant (d) is effected in customary manner, if necessary in the presence of a condensation agent. As condensation agent there come into consideration: when starting from compounds of the formulae VII and VIII in which $Y_1$ represents halogen or etherified hydroxy and $Y_2$ represents a group —A—X—H, or $Y_1$ represents a group —X—A—Y and $Y_2$ represents hydrogen, or $Y_1$ represents a group —X—H and $Y_2$ represents a group —A—Y, for example, basic condensation agents, such as carbonates, hydroxides, alcoholates or amides of alkali metals or alkaline earth metals, for example sodium hydroxide, potassium carbonate, sodium hydride and sodium methoxide, and when starting from compounds VII in which $Y_1$ represents optionally etherified hydroxy, acidic agents, such a mineral acids, for example hydrohalic acids, for example hydrochloric or hydrobromic acid, or sulphuric acid. It is also possible to use the compound VII in which $Y_1$ represents a group —X—H (X=oxy) in the form of a carboxylate salt, for example an alkali metal salt, or to use a compound VIII in which $Y_2$ represents a group —A—X—H (X=oxy) in the form of an alcoholate, for example an alkali metal alcoholate, or to use a compound VII in which $Y_1$ represents a group —X—H (X=imino) or a compound VIII in which $Y_2$ represents hydrogen or a group —A—H—H (X=imino) also in the form of an alkali metal or alkaline earth metal amide.

Starting materials VII in which $Y_1$ represents a group Y, especially etherified hydroxy, or —XH, that is to say hydroxy, amino or lower alkylamino, are almost all known. Novel compounds VII are obtained, for example, by (da) reacting a compound of the formula

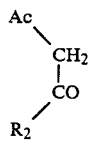 (IIa)

with a compound of the formula

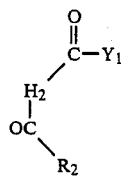 (VIIa)

and with ammonia or an agent yielding ammonia, or (db) reacting a compound of the formula R—CHO (III), or a reactive functional derivative thereof, with a compound of the formula

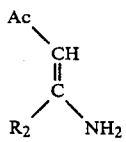 (IIc)

and with a compound IIb, or (dc) reacting a compound III, or a reactive derivative thereof, with a compound of the formula

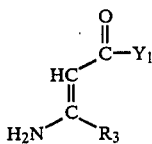

(VIIb)

and with a compound of the formula IIa or IIc.

Compounds VII in which $Y_1$ represents halogen, such as chlorine, are obtained, for example:

(dd) by reaction of a corresponding carboxylic acid (VII; $Y_1=OH$), for example, with thionyl chloride.

Compounds VII in which $Y_1$ represents a group —X—A—Y are obtained, for example:

(de) by reaction of a corresponding carboxylic acid (VII; $Y_1=OH$) or a corresponding carboxylic acid ester or halide (VII; $Y_1=$ etherified hydroxy, halogen) with a compound of the formula H—X—A—Y (VIIc) or with a compound of the formula H—X—A—OH (VIId), respectively, and subsequent conversion of the hydroxy group into a group Y.

In radicals $Y_3$ and $Y_4$ in starting materials IX and X, respectively, in accordance with process variant (e), removable radicals $Y_6$ are, for example, reactive esterified hydroxy groups, such as hydroxy groups esterified by a mineral acid, for example a hydrohalic acid, or by a sulphonic acid, for example an alkanesulphonic acid or a halosulphonic acid or an optionally substituted benzenesulphonic acid, for example chlorine, bromine or iodine, methane- or ethanesulphonyloxy, fluorosulphonyloxy, benzene-, p-bromobenzene- or p-toluenesulphonyloxy.

The reaction of compounds IX and X is effected in a manner known per se, and, especially when using a starting material having a reactive esterified hydroxy group, the reaction is advantageously carried out in the presence of a basic agent, such as an inorganic base, for example an alkali metal or alkaline earth metal carbonate or hydroxide, or an organic basic agent, such as an alkali metal lower alkoxide, and/or an excess of the basic reactant and customarily in the presence of a solvent or solvent mixture and, if necessary, while cooling or heating, for example in a temperature range of from approximately $-20°$ to approximately $+150°$ C., in an open or closed vessel and/or in an inert gas atmosphere, for example in a nitrogen atmosphere.

Starting materials of the formula IX are manufactured, for example, by reacting a compound of the formula

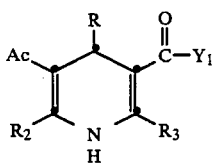

(VII)

in which $Y_1$ represents optionally etherified or esterified hydroxy, for example hydroxy, lower alkoxy or halogen, with a compound of the formula H—X—A—NH$_2$ (IXa) and, if required, then with a compound of the formula

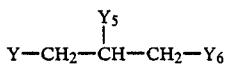

(IXb)

in which Y represents especially halogen, such as chlorine or bromine, for example with epichlorohydrin or epibromohydrin. In analogous manner, also compounds X in which $Y_4$ represents a group of the formula XI are obtained by reaction of compounds X in which $Y_4$ represents hydrogen with a compound IXb.

Compounds of the formula I obtainable according to the process can be converted into different compounds of the formula I in a manner known per se, for example by conversion of substituents present in compounds of the formula I into different substituents covered by the formula I.

Thus, for example, a lower alkoxycarbonyl group Ac can be converted by transesterification into a different lower alkoxycarbonyl group. The reaction is carried out, for example, in an excess of lower alkanol and/or in an inert organic solvent that preferably has a boiling point above the boiling point of the lower alkanol to be freed, and preferably in the presence of a catalyst, for example an alkali metal lower alkoxide, such as sodium or potassium methoxide or ethoxide, or an acidic medium, for example hydrochloric or sulphuric acid, at elevated temperature and, customarily, while distilling off the alcohol freed.

Furthermore, compounds of the formula I in which R represents a pyridyl radical can be converted into corresponding N-oxides. The oxidation can be carried out in a manner known per se, for example by treatment with organic peracids, such as lower alkaneperacids or arene-peracids, such as optionally suitably substituted perbenzoic acids, for example peracetic or 3-chloroperbenzoic acid, preferably at room temperature or at a reaction temperature slightly above room temperature, or with aqueous hydrogen peroxide, for example at temperatures of up to 100° C., in the presence or absence of lower alkanoic acids, for example acetic acid. Care should be taken, especially when using peracids, that overoxidation does not occur as a result of too long a reaction time.

Thio can, for example, be oxidised in customary manner to corresponding sulphinyl or sulphonyl. As suitable oxidising agents for the oxidation to the sulphoxide stage there come into consideration, for example, inorganic peracids, such as peracids of mineral acids, for example periodic acid or persulphuric acid, organic peracids, such as corresponding percarboxylic or persulphonic acids, for example performic, peracetic, trifluoroperacetic, p-nitroperbenzoic, m-chloroperbenzoic or perbenzoic acid or p-toluenepersulphonic acid, or mixtures of hydrogen peroxide and acids, for example a mixture of hydrogen peroxide with acetic acid. The oxidation is often carried out in the presence of suitable catalysts; as catalysts there may be mentioned suitable acids, such as optionally substituted carboxylic acids, for example acetic acid or trifluoroacetic acid, or transition metal oxides, such as oxides of elements of sub-group V or VI, for example vanadium, molybdenum or tungsten oxide. The oxidation is carried out under mild conditions, for example at temperatures of from $-50°$ to approximately $+100°$ C. The oxidation to the sulphone stage can also be carried out in corresponding manner using dinitrogen tetroxide as catalyst in the presence of oxygen at low tempratures, as may also the direct oxidation of thio to sulphonyl, in which case, however, the oxidising agent is usually used in excess.

If the compounds of the formula (I) contain unsaturated radicals, such as lower alkenyloxy or lower alkynyloxy groupings, these groupings may be converted into saturated radicals in a manner known per se. For example, the hydrogenation of multiple bonds is effected by catalytic hydrogenation in the presence of hydrogenation catalysts, there being suitable for this purpose, for example, noble metals or derivatives thereof, for example oxides, such as nickel, Raney nickel, palladium and platinum oxide, which may be supported on carrier materials, for example on carbon or calcium carbonate. The hydrogenation is preferably carried out at pressures of from 1 to approximately 100 atm. and at temperatures of from approximately −80° to approximately 200° C., especially from room temperature to approximately 100° C. The reaction is advantageously effected in a solvent, such as water, a lower alkanol, for example ethanol, isopropanol or n-butanol, an ether, for example dioxan, or a lower alkanecarboxylic acid, for example acetic acid.

Depending on the reaction conditions, the compounds of the formula I and corresponding starting materials may be obtained in free form or in the form of salts.

Thus, resulting acid addition salts can be converted in a manner known per se, for example by treatment with a base, such as an alkali metal hydroxide, into the free compounds, or, for example, by treatment with suitable acids or derivatives thereof into other salts. Resulting free compounds of the formula I can be converted into their salts, for example by treatment with acids or corresponding anion exchangers.

Owing to the close relationship between the compounds of the formula I in free form and in the form of salts, hereinbefore and hereinafter the free compounds or their salts are to be understood as meaning optionally also the corresponding salts or free compounds, respectively, where appropriate with regard to meaning and purpose.

The novel compounds, including the salts thereof, can also be obtained in the form of their hydrates, or their crystals may include, for example, the solvent used for crystallisation.

Compounds of the formula I may, depending upon chemical structure, process reaction and/or nature of the starting materials, form stereoisomers. Depending upon the starting material chosen, the above process variants may be carried out in such a manner that the synthesis in question proceeds enantioselectively, that is to say that it is possible to obtain exclusively or predominantly one of the possible enantiomers.

Thus, for example, depending upon the number of asymmetric carbon atoms, there may be obtained, for example, pure enantiomers or diastereoisomers or mixtures thereof, such as enantiomeric or diastereoisomeric mixtures. In this connection mention should be made especially of the carbon atom of the 1,4-dihydropyridine ring bonded to the group R, and to the carbon atoms bonded to the hydroxy group shown in formula I which may, independently of one another, have the R- or S-configuration. Compounds of the formula I that are regarded as preferred are those in which the carbon atom bonded to the radical R has the R-configuration if Ac represents lower alkoxycarbonyl or lower alkanoyl, or has the S-configuration if Ac represents lower alkanesulphonyl. The carbon atom bonded to the hydroxy group preferably has the S-configuration.

Resulting mixtures of diastereoisomers can be separated into the pure diastereoisomers in known manner on the basis of the physico-chemical differences between the racemates, for example by chromatography and/or fractional crystallisation.

Enantiomeric mixtures can be resolved into the enantiomers (optical antipodes) according to methods known per se, for example by recrystallisation from an optically active solvent, chromatography on chiral absorbents, by cleaving with specific, immobilisable enzymes, via the formation of inclusion compounds, for example using chiral Crown ethers, in which case only one enantiomer is complexed, with the aid of suitable microorganisms or by reaction of a compound of the formula I having salt-forming, for example basic, properties with an optically active, salt-forming agent, such as an optically active acid, and separation of the mixtures of salts obtained in this manner, for example on the basis of their different solubilities, into the diastereoisomeric salts from which the antipodes can be freed, for example by treatment with a base.

It is also possible, however, to start from starting materials, for example II, IV, V, VII and VIII or IX and X, or their precursors having the desired configuration and thus to obtain target compounds having the desired stereogeometry or to use asymmetric synthesis methods.

Furthermore, for example, compounds of the formula I in which Ac represents lower alkoxycarbonyl can be transesterified using an optically active alcohol in accordance with the process described above, and the resulting diastereoisomeric mixture can be separated into the diastereoisomers, for example by means of fractional crystallisation, and the desired enantiomer can be freed by transesterification with a lower alkanol corresponding to the desired lower alkoxycarbonyl group.

The invention relates also to those embodiments of the process according to which a compound obtainable as an intermediate at any stage of the process is used as starting material and the remaining steps are carried out, or a starting material is used in the form of a derivative, for example a salt, and/or its racemate or antipode, or is formed under the reaction conditions. Salts of starting materials having salt-forming basic properties are, for example, those with mineral acids, such as hydrochloric acid, sulphuric acid or phosphoric acid, or with organic acids, for example acetic acid.

In the processes of the present invention there are preferably used those starting materials which result in the compounds described at the beginning as being especially valuable. The present invention relates also to novel starting materials and intermediates and to processes for the manufacture thereof.

In this connection, special mention is made of compounds of the formula IX in which $Y_3$ represents hydrogen, that is to say compounds of the formula

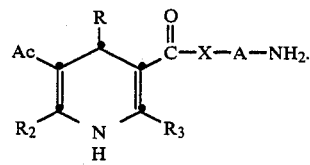

(IXc)

These compounds and their pharmaceutically acceptable salts have valuable pharmacological properties, especially in the cardiovascular field. They exhibit especially antihypertensive activity which can be demonstrated, for example, in renally hypertensive rats with the aid of the test arrangement described by Goldblatt et al. (J. Exptl. Med. 59, 347 (1934)) in doses of approximately from above 30 mg/kg to above 100 mg/kg p.o..

Thus, for example, oral administration of 100 mg/kg of 1,4-dihydro-2,6-dimethyl-4-(3-nitrophenyl)-pyridine-3,5-dicarboxylic acid 3-{2-[p-(2-aminoethoxy)-phenoxy]-ethyl}ester 5-methyl ester to renally hypertensive rats brings about a lowering of blood pressure of approximately 52 mm Hg. The novel compounds also act as calcium-antagonists, as can be demonstrated, for example, in in vitro tests by the inhibition of calcium-induced vasoconstriction in the isolated perfused mesenteric layer of rats, for example using 1,4-dihydro-2,6-dimethyl-4-(m-nitrophenyl)-pyridine-3,5-dicarboxylic acid 3-{2-[p-(2-aminoethoxy)-phenoxy]-ethyl}ester 5-methyl ester at a concentration of approximately 0.2 nmol/liter.

Furthermore, the bonding of the novel compounds to dihydropyridine receptors can be demonstrated by the displacement of the bonding of $^3$H-nitrendipine to the membranes of guinea pig hearts in in vitro tests, for example at a concentration of approximately 0.2 nmol/liter using 1,4-dihydro-4-(3-nitrophenyl)-2,6-dimethyl-pyridine-3,5-dicarboxylic acid 3-{2-[p-(2-aminoethoxy)-phenoxy]-ethyl}ester 5-methyl ester. The compounds of the formula IXc can accordingly be used not only as intermediates for the manufacture of other pharmacologically active compounds, for example those of the formula I, but may also be used as cardiotonics, such as coronary dilators and antihypertensives for the treatment of cardiovascular conditions, such as *Angina pectoris* and its sequelae, vascular spasms, high blood pressure and cardiac insufficiency, and for the manufacture of antianginals, vasodilators, antihypertensives and/or inotropics.

The invention therefore relates also to the use of compounds of the formula IXc in which Ac represents lower alkoxycarbonyl, lower alkanoyl or lower alkanesulphonyl, X represents oxy, imino or lower alkylimino, A represents an alkylene radical interrupted by a group of the formula —$X_1$—Ph—$X_2$ in which at least one of the radicals $X_1$ and $X_2$ represents oxy and a radical $X_1$ or $X_2$ that is other than oxy represents a direct bond, and Ph represents a phenylene radical that is unsubstituted or is substituted by lower alkyl, lower alkoxy, halogen, trifluoromethyl and/or by nitro, and R represents a phenyl radical optionally substituted by lower alkyl, by lower alkoxy, by halo-lower alkoxy, by lower alkenyloxy, by halogen, by trifluoromethyl, by cyano, by an optionally lower alkyl-, lower alkoxy-, halo-, trifluoromethyl- and/or nitro-substituted benzylthio or benzyloxy radical and/or by nitro, or represents an optionally 1-oxidised pyridyl radical optionally substituted by lower alkyl, lower alkoxy, optionally S-oxidised lower alkylthio and/or by halogen, or represents a benzofurazanyl radical, $R_2$ represents lower alkyl and $R_3$ represents lower alkyl, hydroxy-lower alkyl, cyano or amino, and acid addition salts thereof, as intermediates and as active ingredients in medicaments, and to the above compounds themselves where novel, and to processes for their manufacture.

Ac, X, A, R, $R_2$ and $R_3$ have, for example, the meanings given under formula I, especially for the groups of compounds of the formula I described at the beginning as being preferred.

The invention relates also to the use of compounds of the formulae I and IXc, or pharmaceutically acceptable salts of such compounds having salt-forming properties, especially as pharmacologically active compounds, more especially as coronary dilators and antihypertensives for the treatment of cardiovascular conditions, such as *Angina pectoris* and its sequelae, vascular constrictions, high blood pressure and cardiac insufficiency. They may be used, preferably in the form of pharmaceutical preparations, in a method for the prophylactic and/or therapeutic treatment of the animal and human body, especially for the treatment of cardiovascular conditions, such as *Angina pectoris* and its sequelae, vascular constrictions, high blood pressure and cardiac insufficiency.

The dosage of the active ingredient, which is administered on its own or together with a customary carrier and adjunct, depends on the species to be treated, its age and individual condition, and on the method of administration. For example, the daily doses for mammals with a body weight of approximately 70 kg, depending on the nature of the illness, the individual condition and age, are preferably approximately from 100 to 1000 mg, especially from approximately 150 mg to approximately 500 mg, and specifically from approximately 150 mg to 250 mg, in the case of oral administration.

The invention relates also to pharmaceutical preparations that contain as active ingredients compounds of the formula I or IXc, or pharmaceutically acceptable salts of such compounds having salt-forming properties, to processes for their manufacture and to the use of compounds of the formula I or their pharmaceutically acceptable salts for the manufacture of medicaments, as coronary dilators and anti-hypertensives for the treatment of cardiovascular conditions, such as *Angina pectoris* and its sequelae, vascular constrictions, central and peripheral circulation disorders, high blood pressure, arrhythmia and cardiac insufficiency, and also for use as inhibitors of platelet aggregation.

The pharmaceutical preparations according to the invention are for enteral, such as peroral or rectal, and also for sublingual and for parenteral administration to warm-blooded animals. Suitable dosage unit forms, especially for peroral and/or sublingual administration, for example dragées, tablets or capsules, preferably contain from approximately 10 mg to approximately 300 mg, especially from approximately 20 mg to approximately 200 mg, of a compound of the formula I, or a pharmaceutically acceptable salt of a corresponding compound capable of salt formation, together with pharmaceutically acceptable carriers.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes using, for example, corn, wheat, rice or potato starch, gelatine, tragacanth, methyl cellulose and/or, if desired, disintegrators, such as the above-mentioned starches, also carboxymethyl starch, crosslinked polyvinylpyrrolidone, agar-agar, alginic acid or a salt thereof, such as sodium alginate. Adjuncts are especially flow-regulating agents and lubricants, for example silica, talc, stearic acid or salts thereof, such as magnesium or calcium stearate, and/or polyethylene glycol. Dragée cores may be provided with suitable coatings that may be resistant to gastric juices, there being used, inter alia, concentrated sugar solutions which may contain gum arabic, talc, polyvinylpyrrolidone, polyethylene glycol and/or titanium dioxide, or lacquer solutions in suitable organic solvents or solvent mixtures or, for the manufacture of coatings that are resistant to gastric juices, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Other orally administrable pharmaceutical preparations are dry-filled capsules made of gelatine, and also soft, sealed capsules made of gelatine and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, it likewise being possible for stabilisers to be added. Preferred are, inter alia, capsules that can be both easily bitten through, in order to achieve action that is as rapid as possible by sublingual absorption of the active ingredient, and swallowed without being chewed.

There come into consideration as rectally administrable pharmaceutical preparations, for example, suppositories that consist of a combination of the active ingredient with a suppository base. Suitable suppository bases are, for example, natural or synthetic triglycerides, paraffin hydrocarbons, polyethylene glycols or higher alkanols. It is also possible to use gelatine rectal capsules that contain a combination of the active ingredient with a base material; there come into consideration as base materials, for example, liquid triglycerides, polyethylene glycols or paraffin hydrocarbons.

For parenteral administration there are suitable especially aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate, or triglycerides, or aqueous injection suspensions that contain viscosity-increasing substances, for example sodium carboxymethylcellulose, sorbitol and/or dextran, and optionally stabilisers.

The pharmaceutical preparations of the present invention can be manufactured in a manner known per se, for example by means of conventional mixing, granulating, confectioning, dissolving or lyophilising processes. For example, pharmaceutical preparations for oral administration can be obtained by combining the active ingredient with solid carriers, optionally granulating a resulting mixture, and processing the mixture or granulate, if desired or necessary, after the addition of suitable adjuncts, to form tablets or dragée cores.

The following Examples serve to illustrate the invention; temperatures are given in degrees Celsius.

EXAMPLE 1

A mixture of 4.1 g (8.3 mmol) of 1,4-dihydro-2,6-dimethyl-4-(m-nitrophenyl)-pyridine-3,5-dicarboxylic acid 3-{2-[p-(2-aminoethyl)-phenoxy]-ethyl}-ester 5-methyl ester and 1.6 g of 2-(2,3-epoxypropoxy)-benzonitrile in 20 ml of isopropanol is heated under reflux for 2 hours and then concentrated to dryness by evaporation under reduced pressure. The residue is dissolved in 20 ml of 1N methanesulphonic acid and extracted with 40 ml of ethyl acetate. The aqueous phase is separated off and rendered alkaline with 2N sodium hydroxide solution. The crude product obtained by extraction with ethyl acetate is "flash" chromatographed over silica gel using toluene/isopropanol/concentrated ammonia (170:30:3) as eluant. 1,4-dihydro-2,6-dimethyl-4-(m-nitrophenyl)-pyridine-3,5-dicarboxylic acid 3-{{{2-{{p-{2-[3-(o-cyanophenoxy)-2-hydroxypropylamino]-ethyl}-phenoxy}}-ethyl}}}-ester 5-methyl ester is obtained in the form of an amorphous foam.

$^1$H-NMR (CDCl$_3$): 2.3 (6, 2 s); 2.5–3.0 (6, m); 3.0–3.1 (3, m); 3.63 (3, s); 4.0–4.2 (4, m); 4.2–4.4 (2, m); 4.4–4.5 (1, m); 5.1 (1, s); 6.0 (1, s); 6.75 (2, d, 9 Hz); 7.0 (2, m); 7.15 (2, d, 9 Hz); 7.3 (1, 5, 7 Hz); 7.5–7.55 (2, m); 7.63 (1, d, 7 Hz); 7.9 (1, 2d, 2 Hz, 7 Hz); 8.05 (1, m).

The ester required as starting material can be manufactured in the following manner:

(1a) 24.2 g (177 mmol) of tyramine are reacted in 180 ml of dioxan with 39.0 g of pyrocarbonic acid ditertiary butyl ester. After 2 to 3 hours, the dioxan is evaporated off in vacuo. The residue of crude N-tertiary butoxycarbonyltyramine which remains forms an oil which gradually solidifies to crystals and can be used in the following reaction in crude form.

(1b) A mixture of 8.6 g (39 mmol) of crude N-tertiary butoxycarbonyltyramine, 27.6 g (200 mmol) of potassium carbonate and 73.3 g (390 mmol) of 1,2-dibromoethane is heated at boiling for 4 hours while stirring. The reaction mixture is cooled, and then 200 ml of water and 400 ml of ethyl acetate are added and the organic phase is separated off. After concentration by evaporation under reduced pressure, a crystalline residue remains which, after recrystallisation from 2-propanol, yields N-tertiary butoxycarbonyl-2-[p-(2-bromoethoxy)-phenyl]-ethylamine, which has a melting point of 70°–72°.

(1c) 3.3 g (100 mmol) of 1,4-dihydro-2.6-dimethyl-4-(m-nitrophenyl)-pyridine-3,5-dicarboxylic acid 3-methyl ester, 3.5 g (10 mmol) of the bromoethoxy compound from step 1b), and 2.8 g (20 mmol) of potassium carbonate are heated at boiling in 50 ml of acetonitrile while stirring and under reflux. After approximately 20 hours, the reaction mixture is filtered and the filtrate is concentrated by evaporation under reduced pressure. The residue is dissolved in ethyl acetate and washed with water, and the organic phase is concentrated by evaporation in vacuo. Crude 1,4-dihydro-2,6-dimethyl-4-(m-nitrophenyl)-pyridine-3,5-dicarboxylic acid 3-{2-[p-(2-tertiary butoxycarbonylaminoethyl)-phenoxy]-ethyl}-ester 5-methyl ester is thus obtained and is used further in crude form.

(1d) 5.95 g (10 mmol) of the tertiary butoxycarbonyl derivative described in step (c) are dissolved in 30 ml of formic acid. The solution is allowed to stand at 20°–25° for 15 hours and is then concentrated by evaporation in vacuo. The residue is dissolved in 100 ml of 0.1N HCl, the solution is extracted with 100 ml of toluene, and the aqueous phase is rendered alkaline with 2N sodium hydroxide solution. 1,4-dihydro-2,6-dimethyl-4-(m-nitrophenyl)-pyridine-3,5-dicarboxylic acid 3-{2-[p-(2-amimoethyl)-phenoxy]-ethyl}-ester 5-methyl ester is obtained in the form of a yellow foam by extraction with ethyl acetate and concentration of the solution by evaporation. The compound forms a hydrochloride having a melting point of 196°–198° (from isopropanol).

EXAMPLE 2

A solution of 3.5 g (6.8 mmol) of 1,4-dihydro-2,6-dimethyl-4-(m-nitrophenyl)-pyridine-3,5-dicarboxylic acid 3-{2-[p-(2-aminoethoxy)-phenoxy]-ethyl}-ester 5-methyl ester and 1.55 g (8.9 mmol) of 2-(2,3-epoxypropoxy)-benzonitrile in 20 ml of isopropanol is heated under reflux for 2 hours. The oil obtained after concentration by evaporation (approximately 6 g) is purified by "flash" chromatography analogously to Example 1 and yields 1,4-dihydro-2,6-dimethyl-4-(m-nitrophenyl)-pyridine-3,5-dicarboxylic acid 3-{{{2-{{p-{2-[3-(o-cyanophenoxy)-2-hydroxypropylamino]-ethoxy}-phenoxy}}-ethyl}}}-ester 5-methyl ester in the form of an amorphous solid.

$^1$H-NMR (CDCl$_3$): 2.3 (6, 2 s); 3.0–3.1 (4, m); 3.6 (3, s); 4.05 (4, m); 4.14 (3, s); 4.3–4.5 (2, m); 5.1 (1, s); 5.85 (1, s); 6.76 (2, d, 10 Hz); 6.83 (2, d, 10 Hz); 7.0 (2, t, 8 Hz); 7.2–7.3 (1, m); 7.5 (2, m); 7.6 (1,2d, 10 Hz, 2H$_2$); 7.9 (1, m); 8.05 (1, m).

The starting material can be manufactured in the following manner:

(2a) 38.4 g (250 mmol) of 4-(2-aminoethoxy)-phenol are stirred for 2 hours at room temperature with 54.7 g (250 mmol) of pyrocarbonic acid ditertiary butyl ester in 500 ml of dioxan. After the addition of 20 ml of concentrated ammonia, the whole is stirred for a further 30 minutes. After concentration by evaporation under reduced pressure, the residue is dissolved in ethyl acetate and washed with water, and the organic phase is dried (MgSO$_4$) and concentrated by evaporation. The resulting oily crude product is recrystallised from cyclohexane/ether (10:1) and yields p-(2-tertiary butoxycarbonylaminoethoxy)-phenol, which has a melting point of 84°–85°.

(2b) 45.5 g (180 mmol) of the phenol derivative obtained under 2a), 340 g (1.8 mol) of 1,2-dibromoethane and 124 g (0.9 mol) of potassium carbonate are heated at boiling for 7 hours while stirring and under reflux. After cooling, the whole is filtered and the filtrate is diluted with 1 liter of ethyl acetate, washed with 300 ml of water, dried over magnesium sulphate and concentrated to dryness by evaporation under reduced pressure. The crystalline crude product is recrystallised from isopropanol and yields 1-(2-bromoethoxy)-4-(2-tertiary butoxycarbonylaminoethoxy)-benzene, which has a melting point of 84°–85°.

(2c) 8.7 g (24 mmol) of the bromine derivative obtained in step 2b), 8.0 g (24 mmol) of 1,4-dihydro-2,6-dimethyl-4-(m-nitrophenyl)-3,5-pyridine-dicarboxylic acid monomethyl ester and 6.6 g (48 mmol) of potassium carbonate are heated at boiling in 100 ml of acetonitrile for 20 hours while stirring and under reflux. Working up analogously to Example 1c yields 1,4-dihydro-2,6-dimethyl-4-(m-nitrophenyl)-pyridine-3,5-dicarboxylic acid 3-{2-[p-(2-tertiary butoxycarbonylaminoethoxy)-phenoxy]-ethyl}-ester 5-methyl ester, which is used in the following step without being purified further.

(2d) 14.6 g of the product obtained in step (2c) are dissolved in 50 ml of formic acid. The solution is allowed to stand for 6 hours at room temperature and is worked up analogously to Example (1d). A crystalline crude product is thus obtained, which, after recrystallisation from acetonitrile, yields 1,4-dihydro-2,6-dimethyl-4-(m-nitrophenyl)-pyridine-3,5-dicarboxylic acid 3-{2-[p-(2-aminoethoxy)-phenoxy]-ethyl}-ester 5-methyl ester, which has a melting point of 153°–154°.

EXAMPLE 3

A solution of 5.4 g (10 mmol) of 1,4-dihydro-2,6-dimethyl-4-(m-nitrophenyl)-pyridine-3,5-dicarboxylic acid 3-{2-[p-(2-amino-2-methylpropoxy)-phenoxy]-ethyl}-ester 5-methyl ester and 2.3 g (13 mmol) of 2-(2,3-epoxypropoxy)-benzonitrile in 30 ml of isopropanol is heated under reflux for 18 hours. After working up and chromatography analogously to Example 1, 1,4-dihydro-2,6-dimethyl-4-(m-nitrophenyl)-pyridine-3,5-dicarboxylic acid 3-{{{2-{{p-{2-[3-(o-cyanophenoxy)-2-hydroxypropylamino]-2-methylpropoxy}-phenoxy}}-ethyl}}}-ester 5-methyl ester is obtained in the form of an amorphous solid.

$^1$H-NMR (DMSO-d$_6$): 1.1 (6, s); 1.9 (1, b); 2.3 (6, 2s); 2.6–2.8 (2, m); 3.52 (3, s); 3.67 (2, s); 3.85 (1, b); 4.0–4.1 (4, m); 4.1–4.2 (2, b); 5.0 (1, s); 5.1 (1, b); 6.80 (2, d, 8 Hz); 6.82 (2, d, 8 Hz); 7.07 (1, t, 7 Hz); 7.24 (1, d, 8 Hz); 7.44 (1, t, 7 Hz); 7.6–7.5 (3, m); 7.94 (1, s); 8.0 (1, m); 10.6 (1, s).

The starting material can be manufactured in the following manner:

(3a) A mixture of 100.0 g (0.5 mol) of hydroquinonemonobenzyl ether, 124 g (0.75 mol) of methanesulphonic acid 2-methyl-2-nitropropyl ester, 207 g of potassium carbonate and 500 ml of dimethylformamide is stirred in a bath of a temperature of 130°–140° for 70–80 hours. After cooling, the whole is filtered and the filtrate is concentrated by evaporation in vacuo. The black oil which remains is dissolved in ethyl acetate (approximately 1 liter) and the solution is extracted with 200 ml of 2N sodium hydroxide solution, washed with water, dried (MgSO$_4$) and concentrated by evaporation. After chromatography over 1 kg of silica gel (elution with ethyl acetate), crude hydroquinone-1-benzyl-4-(2methyl-2-nitropropyl)-ether is obtained, which melts at 75°–76° after recrystallisation from methanol.

(3b) 26 g (86 mmol) of hydroquinone-1-benzyl-4-(2-methyl-2-nitropropyl)-ether are hydrogenated in 400 ml of methanol over 2.6 Pd/C (5%) at 50 bar and 50°–55° until 4 equivalents of hydrogen have been taken up (approximately 16 hours). After filtration and concentration by evaporation, a crystalline residue is obtained which, after recrystallisation from isopropanol, yields hydroquinone-mono-(2-amino-2-methylpropyl)-ether, which has a melting point of 165°–166°.

(3c) Analogously to Example (2a), 13.8 g (76 mmol) of hydroquinone mono-(2-amino-2-methylpropyl)-ether and 16.6 g (76 mmol) of pyrocarbonic acid ditertiary butyl ester are reacted and worked up. After recrystallisation from ether/cyclohexane, p-[2-(tertiary butoxycarbonylamino)-2-methylpropoxy]-phenol, which has a melting point 121°–123°, is obtained.

(3d) Analogously to Example (2b), a mixture of 19.2 g (68 mmol) of p-[2-(tertiary butoxycarbonylamino)-2-methylpropoxy]-phenol, 47 g (340 mmol) of potassium carbonate and 1.5 g of triethylbenzylammonium chloride is reacted in 57 ml (680 mmol) of 1,2-dibromoethane and worked up. Crude 1-(2-bromoethoxy)-4-[2-(tertiary butoxycarbonylamino)-2-methylpropoxy]-benzene is obtained in the form of an oil, which is used further in crude form.

(3e) 16.6 g (50 mmol) of 1,4-dihydro-2,6-dimethyl-4-(m-nitrophenyl)-3,5-pyridine-dicarboxylic acid monomethyl ester, 19.4 g (50 mmol) of crude 1-(2-bromoethoxy)-4-[2-(tertiary butoxycarbonylamino)-2-methylpropoxy]-benzene 13.8 g of potassium carbonate and 0.6 g of triethylbenzylammonium chloride are heated at boiling in 500 ml of acetonitrile for 16 hours while stirring and under reflux. The reaction mixture is filtered, concentrated by evaporation and dissolved in 500 ml of ethyl acetate. After washing with 100 ml of water and drying (MgSO$_4$), the solvent is evaporated off and 50 ml of dioxan and 100 ml of formic acid are added to the crude residue without the latter being further purified, and the whole is left to stand in the dark at room temperature for 7–10 hours. After concentration by evaporation in vacuo, the residue is dissolved in 2N hydrochloric acid and the solution is extracted with toluene. The aqueous phase is rendered alkaline with 2N sodium hydroxide solution and extracted with ethyl acetate. After drying the solution (MgSO$_4$) and concentration by evaporation, an oil is obtained from which 1,4-dihydro-2,6-dimethyl-4-(m-nitrophenyl)-pyridine-3,5-dicarboxylic acid 3-{2-[p-(2-amino-2-methylpropoxy)-phenoxy]-ethyl}-ester 5-methyl ester, which has a melting point of 141°–142°, is obtained from acetonitrile.

EXAMPLE 4

Analogously to Example 3, 2.7 g (5 mmol) of 1,4-dihydro-2,6-dimethyl-4-(m-nitrophenyl)-pyridine-3,5-dicarboxylic acid 3-{2-[p-(2-amino-2-methylpropoxy)-phenoxy]-ethyl-}-ester 5-methyl ester and 1.46 g (6.5 mmol) of 1-(2,3-epoxypropoxy)-4-(2-methoxyethoxy)-benzene in 20 ml of isopropanol are reacted and worked up. After "flash" chromatography on silica gel using a mixture of toluene/isopropanol/-concentrated ammonia (170:30:3), 1,4-dihydro-2,6-dimethyl-4-(m-nitrophenyl)-pyridine-3,5-dicarboxylic acid 3-{{{2-{{p-{2-[[3-[p-(2-methoxyethoxy)-phenoxy]-2-hydroxypropylamino]]-2-methylpropoxy}-phenoxy}}-ethyl}}}-ester 5-methyl ester is obtained in the form of an amorphous foam.

$^1$H-NMR (DMSO-d$_6$): 1.1 (6, s); 2.28 (6, 2s); 2.5–2.7 (2, m); 3.28 (3, s); 3.52 (3, s); 3.58–3.68 (4, m); 3.7–3.8 (3, m); 4.0–4.1 (4, m); 4.25 (2, m); 5.0 (1, s); 5.0 (1, b); 6.80–6.85 (4, m); 7.45 (1, t); 7.6 (1, d); 7.94 (2, m); 9.1 (1, s).

EXAMPLE 5

The following are obtained in a manner analogous to that described in Examples 1 to 4:
1,4-dihydro-4-(m-nitrophenyl)-2,6-dimethylpyridine-3,5-dicarboxylic acid 3-{{{2-{{p-{2-[3-(o-cyanophenoxy)-2-hydroxypropylamino]-propoxy}-phenoxy}}-ethyl}}}-ester 5-methyl ester;
1,4-dihydro-4-(m-nitrophenyl)-2,6-dimethylpyridine-3,5-dicarboxylic acid 3-{{{2-{{o-{2-[3-(o-cyanophenoxy)-2-hydroxypropylamino]-ethoxy}-phenoxy}}-ethyl}}}-ester 5-methyl ester;
1,4-dihydro-4-(m-nitrophenyl)-2,6-dimethylpyridine-3,5-dicarboxylic acid 3-{{{2-{{p-{2-[[3-[p-(2-methoxyethoxy)-phenoxy]-2-hydroxypropylamino]]-ethoxy}-phenoxy}}-ethyl}}}-ester 5methyl ester;
1,4-dihydro-4-(m-nitrophenyl)-2,6-dimethylpyridine-3,5-dicarboxylic acid 3-{{{2-{{p-{2-[[3-[p-(2-isopropoxyethoxymethyl)-phenoxy]-2-hydroxypropylamino]]-ethoxy}-phenoxy}}-ethyl}}}-ester 5-methyl ester;
1,4-dihydro-4-(m-methoxyphenyl)-2,6-dimethylpyridine-3,5-dicarboxylic acid 3-{{{3-{{p-{2-[3-(o-cyanophenoxy)-2-hydroxypropylamino]-ethoxy}-phenoxy}}-propyl}}}-ester 5-methyl ester; and
1,4-dihydro-4-(m-nitrophenyl)-2,6-dimethylpyridine-3,5-dicarboxylic acid 3-{{{3-{{p-{2-[3-(o-cyanophenoxy)-2-hydroxypropylamino]-ethoxy}-phenoxy}}-propyl}}}-ester 5-methyl ester.

EXAMPLE 6

A solution of 4.6 g (8.5 mmol) of 1,4-dihydro-2,6-dimethyl-4-(m-nitrophenyl)-pyridine-3,5-dicarboxylic acid 3-{2-[p-(2-amino-2-methylpropoxy)-phenoxy]-ethyl}-ester 5-methyl ester and 2.95 g (11 mmol) of 1-(2,3-epoxypropoxy)-4-[2-(isopropoxy)-ethoxymethyl]-benzene in 20 ml of isopropanol is heated under reflux for 6 hours while stirring. Working up and chromatographic purification analogously to Example 1 yield 1,4-dihydro-2,6-dimethyl-4-(m-nitrophenyl)-pyridine-3,5-dicarboxylic acid 3-{{{2-{{p-{2-[[3-[4-(2-isopropoxyethoxymethyl)-phenoxy]-2-hydroxypropylamino]]-2-methylpropoxy}-phenoxy}}-ethyl}}}-ester 5-methyl ester in the form of a vitreous solid having the structure:

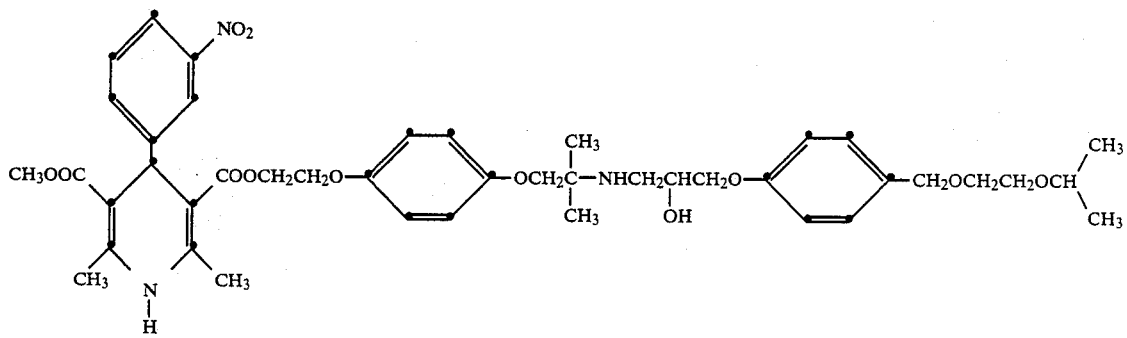

$^1$H-NMR (DMSO-d$_6$): 1.06–1.12 (12, 1s+1d); 2.30 (6, 2s); 2.5–2.7 (2, m); 3.48 (3, s); 3.53 (3, s); 3.67 (2, s); 3.7∝4.3 (7, m); 4.40 (2, s); 5.0 (2, s+b); 6.7–8.0 (12 arom. H); 9.1 (1 NH, s).

EXAMPLE 7

A solution of 5.11 g (10 mmol) of 1,4-dihydro-2,6-dimethyl-4-(m-nitrophenyl)-pyridine-3,5-dicarboxylic acid 3-{2-[p-(2-aminoethoxy)-phenoxy]-ethyl}-ester 5-methyl ester and 3.2 g (12 mmol) of 1-(2,3-epoxypropoxy)-4-[2-(isopropoxy)-ethoxymethyl]-benzene in 30 ml of isopropanol is heated at boiling for 4 hours while stirring and under reflux. After the solvent has been evaporated off, the residue is "flash" chromatographed on 1 kg of silica gel (toluene, isopropanol, concentrated ammonia 170:30:3). The fractions containing the desired product are concentrated by evaporation and yield 1,4-dihydro-2,6-dimethyl-4-(m-nitrophenyl)-pyridine-3,5-dicarboxylic acid 3-{{{2-{{p-{2-[[3-[4-(2-isopropoxyethoxymethyl)-phenoxy]-2-hydroxyproylamino]]-ethoxy}-phenoxy}}-ethyl}}}-ester 5-methyl ester in the form of a vitreous solid having the structure

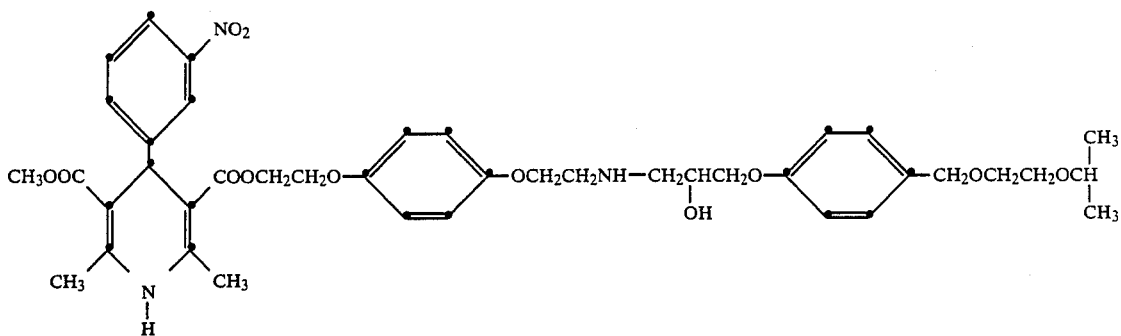

$^1$H-NMR (DMSO-d$_6$): 1.15 (6, d); 2.30 (6, 2s); 2.6–2.8 (2, m); 2.90 (2, t); 3.50 (3, s); 3.55 (4, s); 3.50–3.58 (1, m); 3.9–4.0 (6, m); 4.1 (2, m); 4.3 (2, m); 5.0 (1, s); 5.1 (1, b); 6.7–7.95 (12 arom. H); 9.1 (1, s).

EXAMPLE 8

1,4-dihydro-2,6-dimethyl-4-(m-nitrophenyl)-pyridine-3,5-dicarboxylic acid 3-{{{2-{{p-{2-[[3-[4-(2-methoxyethyl)-phenoxy]-2-hydroxypropylamino]]-ethoxy}-phenoxy}}-ethyl}}}-ester 5-methyl ester can be manufactured analogously to Example 7 in the form of a viscous oil:

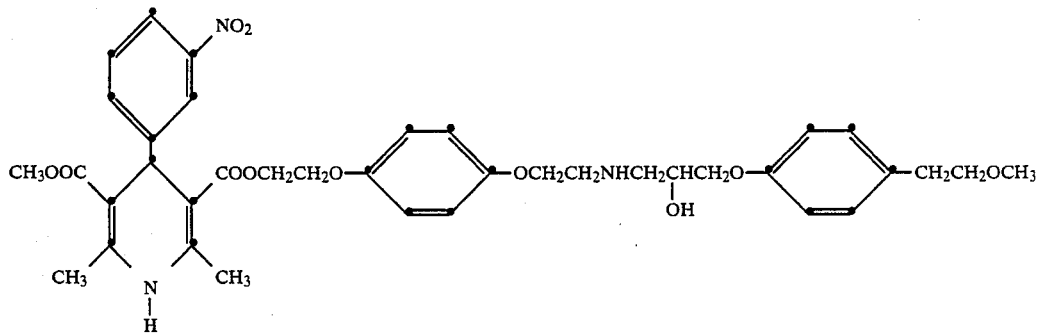

$^1$H-NMR (DMSO-d$_6$): Analogous to Example 7, differing signals at 2.72 ppm (2, t) ArCH$_2$CH$_2$—O; 3.46 (2, t) ArCH$_2$CH$_2$O—; 3.21 (3, s, ) —OCH$_3$.

EXAMPLE 9

1,4-dihydro-2,6-dimethyl-4-(m-nitrophenyl)-pyridine-3,5-dicarboxylic acid 3-{{{2-{{p-{2-[[3-[4-(2-methoxyethoxy)-phenoxy]-2-hydroxypropylamino]]-ethoxy}-phenoxy}}-ethyl}}}-ester 5-methyl ester can be manufactured analogously to Example 7 in the form of a resin:

$^1$H-NMR (DMSO-d$_6$): Analogous to Example 7; differing signals at 3.28 ppm (3, s) —OCH$_3$; 3.62 (2, t) ArOCH$_2$CH$_2$O—CH$_3$; 3.98 (2, t) ArOCH$_2$CH$_2$OCH$_3$.

EXAMPLE 10

1,4-dihydro-2,6-dimethyl-4-(m-nitrophenyl)-pyridine-3,5-dicarboxylic acid-{{{2-{{p-{2-[[3-[4-(2-cyclopropylmethoxyethyl)-phenoxy]-2-hydroxypropylamino]]-ethoxy}-phenoxy}}-ethyl}}}-ester 5-methyl ester can be manufactured analogously to Example 7 in the form of a resin:

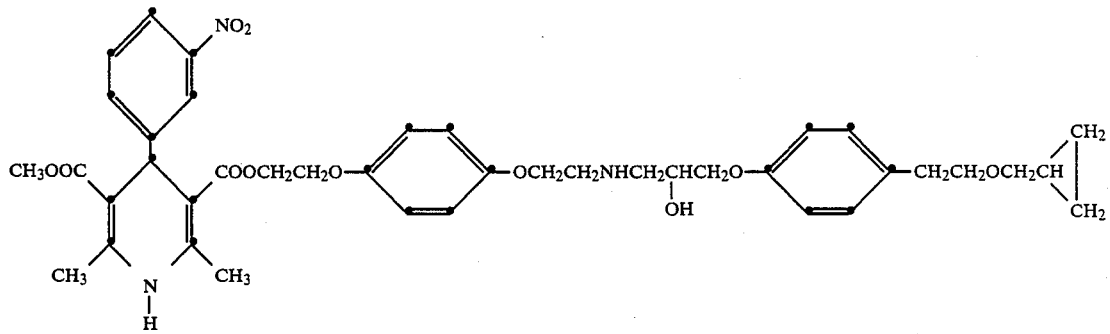

$^1$H-NMR (DMSO-d$_6$): Analogous to Example 7; differing signals at 0.13 ppm (2, m) and 0.44 (2, m)

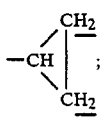

Example 11

1,4-dihydro-2,6-dimethyl-4-(m-nitrophenyl)-pyridine-3,5-dicarboxylic acid 3-{{{2-{{p-{2-[[3-[4-(2-isopropoxyethoxy)-phenoxy]-2-hydroxypropylamino]]-ethoxy}-phenoxy}}-ethyl}}}-ester 5-methyl ester can be manufactured analogously to Example 7 in the form of a resin:

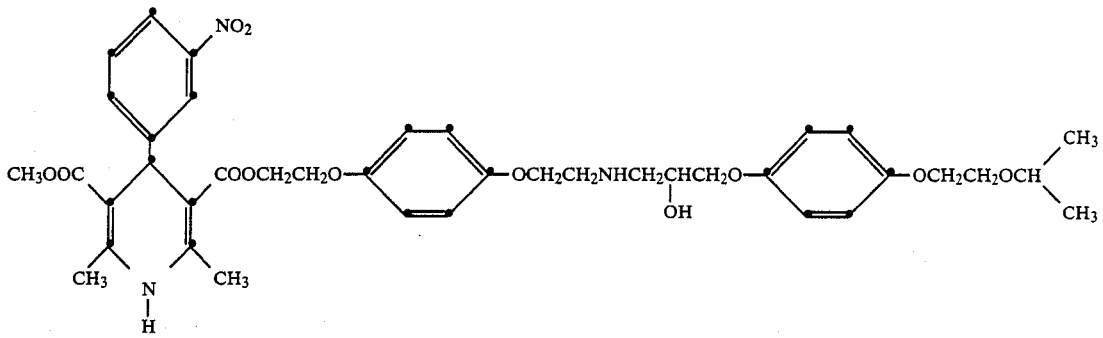

$^1$H-NMR (DMSO-d$_6$): Analogous to Example 7; differing signals at 1.08 (6, d) —CH(CH$_3$)$_2$; 3.56–3.66 (3, m) —CH$_2$OCH.

EXAMPLE 12

A solution of 3.0 g (5.86 mmol) of 1,4-dihydro-2,6-dimethyl-4-(m-nitrophenyl)-pyridine-3,5-dicarboxylic acid 3-{2-[o-(2-aminoethoxy)-phenoxy]-ethyl ester 5-methyl ester and 2.0 g (7.6 mmol) of 1-(2,3-epoxypropoxy)-4-[2-[2-(isopropoxy)-ethoxymethyl]-benzene in 50 ml of isopropanol is heated at boiling for 2 hours while stirring and under reflux. Working up and chromatographic purification analogously to Example 7 yield 1,4-dihydro-2,6-dimethyl-4-(m-nitrophenyl)-pyridine-3,5-dicarboxylic acid 3-{{{2-{{o-{2-[[3-[4-(2-isopropoxyethoxymethyl)-phenoxy]-2-hydroxypropylamino]]-ethoxy}-phenoxy}}-ethyl]]-ester 5-methyl ester in the form of a resinous solid having the structure ester there is obtained o-(2-tertiary butoxycarbonylaminoethoxy)-phenol in the form of an oil which solidifies to crystals and is used further in crude form.

(12b) Reacting crude o-(2-tertiary butoxycarbonylaminoethoxy)-phenol with 1,2-dibromoethane analogously to Example 2 b yields 1-(2-bromoethoxy)-2-(2-tertiary butoxycarbonylaminoethoxy)-benzene, which has a melting point of 74°–75° (from isopropanol).

(12c) and (12d) Analogously to steps (2c) and (2d), 1,4-dihydro-2,6-dimethyl-4-(m-nitrophenyl)-pyridine-3,5-dicarboxylic acid 3-{2-[o-(2-aminoethoxy)-phenoxy]-ethyl ester 5-methyl ester is obtained in the form of a yellow foam from the compound mentioned under 12b after purification by "flash" chromatography (chloroform/methanol 8:1).

EXAMPLE 13

A mixture of 2.0 g (4.0 mmol) of 1,4-dihydro-2,6-dimethyl-4-(m-methoxyphenyl)-pyridine-3,5-dicarboxylic acid 3-{2-[p-(2-aminoethoxy)-phenoxy]-ethyl}-ester ester and 1.4 g (5.2 mmol) of 1-(2,3-epoxypropoxy)-4-[2-(isopropoxy)-ethoxymethyl]-benzene in 10 ml of isopropanol is heated at boiling for 3 hours while stirring and under reflux. Working up analogously to Example 7 yields 1,4-dihydro-2,6-dimethyl-4-(m-methoxyphenyl)-pyridine-3,5-dicarboxylic acid 3-{{{2-{{p-{2-[[3-[4-(2-isopropoxyethoxymethyl)-phenoxy]-2-hydroxypropylamino]]-ethoxy}-phenoxy}}-ethyl}}}-ester 5-methyl ester in the form of a vitreous solid having the structure

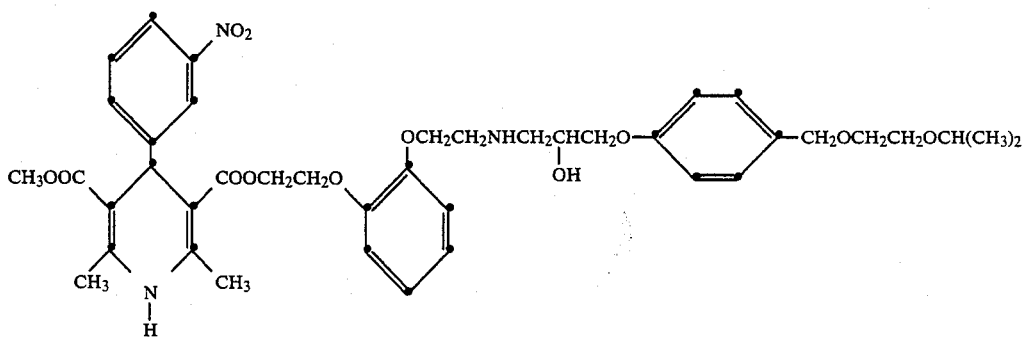

The starting material can be manufactured in the following manner:

(12a) Analogously to Example (2a), from o-(2-aminoethoxy)-phenol and pyrocarbonic acid ditertiary butyl

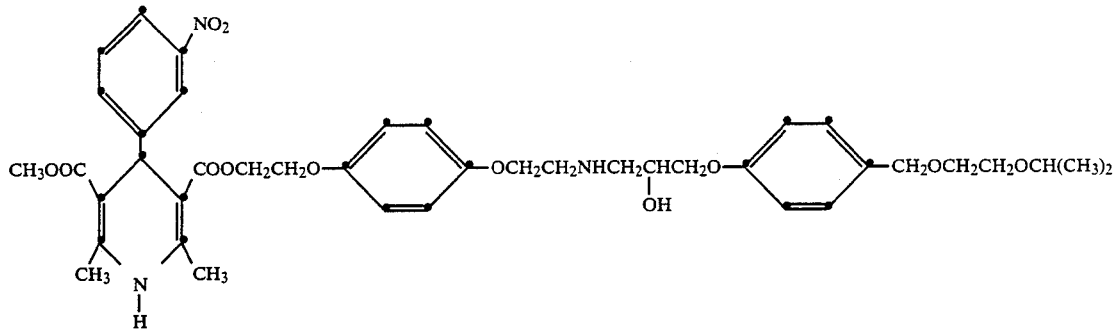

The starting material can be manufactured in the following manner:

(13a) 1,4-dihydro-2,6-dimethyl-4-(m-methoxyphenyl)-3,5-dicarboxylic acid monomethyl ester, which has a melting point of 198°-200° (sinters from 194°) is obtained by a known method from 3-methoxybenzaldehyde, 3-aminocarboxylic acid methyl ester and acetoacetic acid-(2-cyanoethyl ester), and is used further in the form of the crude product.

(13b) Analogously to Examples (2c) and (2d), 1,4-dihydro-2,6-dimethyl-4-(m-methoxyphenyl)-pyridine-3,5-dicarboxylic acid 3-{2-[p-(2-aminoethoxy)-phenoxy]-ethyl}-ester 5-methyl ester, which has a melting point of 144°-146° (from acetonitrile), is obtained from the compound described in (13a).

EXAMPLE 14

The following can be manufactured in a manner analogous to that described in Examples 1–13:

1,4-dihydro-2,6-dimethyl-4-(m-nitrophenyl)-pyridine-3,5-dicarboxylic acid {{{2-{{p-{2-[[3-[4-(2-cyclopropylmethoxyethyl)-phenoxy]-2-hydroxypropylamino]]-2-methylpropoxy}-phenoxy}}-ethyl}}}-ester 5-methyl ester;

1,4-dihydro-2,6-dimethyl-4-(m-methoxyphenyl)-pyridine-3,5-dicarboxylic acid {{{2-{{p-{2-[[3-[4-(2-cyclopropylmethoxyethyl)-phenoxy]-2-hydroxypropylamino]]-ethoxy}-phenoxy}}-ethyl}}}-ester 5-methyl ester;

1,4-dihydro-2,6-dimethyl-4-(m-nitrophenyl)-pyridine-3,5-dicarboxylic acid {{{2-{{m-{2-[[3-[4-(2-isopropoxyethoxymethyl)-phenoxy]-2-hydroxypropylamino]]-ethyl}-phenoxy}}-ethyl}}}-ester 5-methyl ester;

1,4-dihydro-2,6-dimethyl-4-(3-methoxyphenyl)-pyridine-3,5-dicarboxylic acid {{{2-{{p-{2-[[3-[4-(2-methoxyethoxy)-phenoxy]-2-hydroxypropylamino]]-ethoxy}-phenoxy}}-ethyl}}}-ester 5-methyl ester, m.p. 65°-67°;

1,4-dihydro-2,6-dimethyl-4-(3-methoxyphenyl)-pyridine-3,5-dicarboxylic acid {{{2-{{p-{2-[[3-[4-(2-isopropoxyethoxy)-phenoxy]-2-hydroxypropylamino]]-ethoxy}-phenoxy}}-ethyl}}}-ester 5-methyl ester;

1,4-dihydro-2,6-dimethyl-4-(2,3-dichlorophenyl)-pyridine-3,5-dicarboxylic acid {{{2-{{p-{2-[[3-[4-(2-isopropoxyethoxymethyl)-phenoxy]-2-hydroxypropylamino]]-ethoxy}-phenoxy}}-ethyl}}}-ester 5-methyl ester;

1,4-dihydro-2,6-dimethyl-4-(m-nitrophenyl)-pyridine-3,5-dicarboxylic acid {{{2-{{p-{3-[[3-[4-(2-isopropoxyethoxymethyl)-phenoxy]-2-hydroxypropylamino]]-propoxy}-phenoxy}}-ethyl}}}-ester 5-methyl ester;

1,4-dihydro-2,6-dimethyl-4-(m-nitrophenyl)-pyridine-3,5-dicarboxylic acid {{{3-{{p-{2-[[3-[4-(2-isopropoxyethoxymethyl)-phenoxy]-2-hydroxypropylamino]]-ethoxy{-phenoxy{{-propyl}}}-ester 5-methyl ester;

1,4-dihydro-2,6-dimethyl-4-(2-nitrophenyl)-pyridine-3,5-dicarboxylic acid {{{2-{{p-{2-[[3-[4-(2-isopropoxyethoxymethyl)-phenoxy]-2-hydroxypropylamino]]-ethoxy}-phenoxy}}-ethyl}}}-ester 5-methyl ester;

1,4-dihydro-2,6-dimethyl-4-(2-chlorophenyl)-pyridine-3,5-dicarboxylic acid {{{2-{{p-{2-[[3-[4-(2-isopropoxyethoxymethyl)-phenoxy]-2-hydroxypropylamino]]-ethoxy}-phenoxy}}-ethyl}}}-ester 5-methyl ester.

EXAMPLE 15

Tablets which contain 20 mg of active ingredient, for example 1,4-dihydro-4-(m-nitrophenyl)-2,6-dimethyl-pyridine-3,5-dicarboxylic acid 3-{{{2-{{p-{2-[[3-[p-(2-isopropoxyethoxymethyl)-phenoxy]-2-hydroxypropylamino]]-ethoxy}-phenoxy}}-ethyl}}}-ester 5-methyl ester, are manufactured in customary manner in the following composition:

| Composition: | |
|---|---|
| active ingredient | 20 mg |
| wheat starch | 60 mg |
| lactose | 50 mg |
| colloidal silica | 5 mg |
| talc | 9 mg |
| magnesium stearate | 1 mg |
| | 145 mg |

Manufacture

The active ingredient is mixed with a portion of the wheat starch, with the lactose and with the colloidal silica, and the mixture is forced through a sieve. A further portion of the wheat starch is made into a paste with 5 times the amount of water on a water bath, and the powder mixture is kneaded with this paste until a slightly plastic mass has formed.

The plastic mass is pressed through a sieve having a mesh width of approximately 3 mm and dried, and the resulting dry granulate is again forced through a sieve. The remaining wheat starch, and talc and the magnesium stearate are then mixed in and the mixture is compressed to form tablets which each weigh 145 mg and have a breaking notch.

EXAMPLE 16

Tablets which contain 1 mg of active ingredient, for example 1,4-dihydro-4-(m-nitrophenyl)-2,6-dimethylpyridine-3,5-dicarboxylic acid 3-{{{2-{{p-{2-[[3-[p-(2-isopropoxyethoxymethyl)-phenoxy]-2-hydroxypropylamino]]-ethoxy}-phenoxy}}-ethyl}}}-ester 5-methyl ester, are manufactured in customary manner in the following composition:

| Composition: | |
|---|---|
| active ingredient | 1 mg |
| wheat starch | 60 mg |
| lactose | 50 mg |
| colloidal silica | 5 mg |
| talc | 9 mg |
| magnesium stearate | 1 mg |
| | 126 mg |

Manufacture

The active ingredient is mixed with a portion of the wheat starch, with the lactose and with the colloidal silica, and the mixture is forced through a sieve. A further portion of the wheat starch is made into a paste with 5 times the amount of water on a water bath, and the powder mixture is kneaded with this paste until a slightly plastic mass has formed.

The plastic mass is pressed through a sieve having a mesh width of approximately 3 mm and dried, and the resulting dry granulate is again forced through a sieve. The remaining wheat starch, the talc and the magnesium stearate are then mixed in, and the mixture is compressed to form tablets which each weigh 126 mg and have a breaking notch.

EXAMPLE 17

Capsules which contain 10 mg of active ingredient, for example 1,4-dihydro-4-(m-nitrophenyl)-2,6-dimethylpyridine-3,5-dicarboxylic acid 3-{{{2-{{p-{2-[[3-[p-(2-isopropoxyethoxymethyl)-phenoxy]-2-hydroxypropylamino]-ethoxy}-phenoxy}}-ethyl}}}-ester 5-methyl ester, are manufactured in customary manner as follows:

| Composition: | |
|---|---|
| active ingredient | 2500 mg |
| talc | 200 mg |
| colloidal silica | 50 mg |

Manufacture

The active substance is intimately mixed with the talc and the colloidal silica, the mixture is forced through a sieve having a mesh width of 0.5 mm, and the resulting product is introduced in 11 mg portions into hard gelatine capsules of a suitable size.

EXAMPLE 18

It is also possible to manufacture pharmaceutical preparations which, instead of the compound described in Examples 15 to 17, contain as active ingredient a different compound selected from those described in Examples 1 to 14.

What is claimed is:

1. A compound of the formula

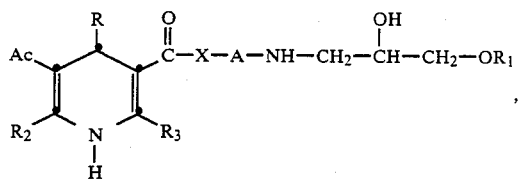

in which Ac represents lower alkoxycarbonyl, lower alkanoyl or lower alkanesulphonyl;

X represents oxy, imino or lower alkylimino; of the formula $-X_1-Ph-X_2-$; in which one of the radicals $X_1$ and $X_2$ is oxy and the other of $X_1$ and $X_2$ is oxy or a direct bond;

Ph represents a phenylene radical that is unsubstituted or is substituted by at least one of lower alkyl, lower alkoxy, halogen, trifluoromethyl and nitro; and R represents a phenyl radical unsubstituted or substituted at least one of lower alkyl, lower alkoxy, halo-lower alkoxy, lower alkenyloxy, halogen, trifluoromethyl, cyano, benzylthio benzyloxy, and nitro, said benzylthio and benzyloxy each independently being unsubstituted or substituted by at least one of lower alkyl, lower alkoxy, halo, trifluoromethyl, and nitro; or R represents pyridyl or 1-oxidized pyridyl, each of which is independently unsubstituted or substituted by at least one of lower alkyl, lower alkoxy, lower alkylthio, S-oxidized lower alkylthio, and halogen; or R represents a (1,3-dioxa)indanyl or benzofuraznyl radical;

$R_1$ represents a phenyl radical unsubstituted or substituted by at least one of lower alkyl, lower alkoxy-lower alkyl, lower alkoxy-lower alkoxy-lower alkyl, cycloalkyl-lower alkoxy-lower alkyl, carbamoyl-lower alkyl, lower alkanoylamino-lower alkyl, lower alkoxy, lower alkenyloxy, lower alkynyloxy, lower alkoxy-lower alkoxy, carbamoyl-lower alkoxy, lower alkanoylamino-lower alkoxy and cyano; or $R_1$ represents an indolyl radical unsubstituted or substituted by lower alkyl;

$R_2$ represents lower alkyl; and $R_3$ represents lower alkyl, hydroxy-lower alkyl, cyano or amino; or an acid addition salt thereof.

2. A compound according to claim 1 of the formula I in which Ac represents $C_1$-$C_7$-alkanoyl, $C_1$-$C_7$-alkoxycarbonyl or $C_1$-$C_4$-alkanesulphonyl;

X represents oxy, imino or $C_1$-$C_4$-alkylimino;

A represents a $C_1$-$C_4$-alkylenephenyleneoxy-$C_2$-$C_4$-alkylene or $C_2$-$C_4$-alkyleneoxyphenylene-$C_1$-$C_4$-alkylene radical having from 8 up to and including 14 members or a $C_1$-$C_4$-alkyleneoxyphenyleneoxy-$C_1$-$C_4$-alkylene radical having from 10 up to and including 14 members, each unsubstituted or substituted in the phenylene moiety by at least one of $C_1$-$C_4$-alkyl, $C_1$-$C_4$-alkoxy, halogen, trifluoromethyl and nitro;

R represents a phenyl radical which is unsubstituted or substituted by at least one of $C_1$-$C_4$-alkyl, $C_1$-$C_4$-alkoxy, mono- up to and including tetra-halo-$C_1$-$C_4$-alkoxy, $C_2$-$C_4$-alkenyloxy, benzylthio, benzyloxy, halogen, trifluoromethyl, cyano and nitro, each of said benzylthio and benzyloxy being independently unsubstituted or substituted by at least one of $C_1$–$C_4$-alkyl, $C_1$–$C_4$-alkoxy, halo, trifluoromethyl, and nitro; or R represents a pyridyl or 1-oxidopyridyl radical, each independently unsubstituted or substituted by at least one of $C_1$–$C_4$-alkyl, $C_1$–$C_4$-alkoxy, $C_1$–$C_4$-alkylthio, $C_1$–$C_4$-alkanesulphinyl, $C_1$–$C_4$-alkanesulphonyl and halogen; or R represents a 4-(1,3-dioxa)indanyl or 8-benzofurazanyl radical;

$R_1$ represents a phenol radical unsubstituted or substituted by at least one of $C_1$–$C_4$-alkyl, $C_1$–$C_4$-alkoxy-$C_2$–$C_4$-alkyl, $C_1$–$C_4$-alkoxy-$C_2$–$C_4$-alkoxy-$C_1$–$C_4$-alkyl, 3- to 5-membered cycloalkyl-$C_1$–$C_4$-alkoxy-$C_2$–$C_4$-alkyl, carbamoyl-$C_1$–$C_4$-alkyl, $C_2$–$C_7$-alkanoyl-amino-$C_1$–$C_4$-alkyl, $C_1$–$C_4$-alkoxy, $C_2$–$C_4$-alkenyloxy, $C_2$–$C_4$-alkynyloxy, omega-$C_1$–$C_4$-alkoxy-$C_2$–$C_4$-alkoxy, carbamoyl-$C_1$–$C_4$-alkoxy, omega-$C_2$–$C_7$-alkanoylamino-$C_2$–$C_4$-alkoxy and cyano; or $R_1$ represents an indolyl radical unsubstituted or substituted by $C_1$–$C_4$-alkyl;

$R_2$ represents $C_1$–$C_4$-alkyl; and $R_3$ represents $C_1$–$C_4$-alkyl, hydroxy-$C_1$–$C_4$-alkyl, cyano or amino;

or an acid addition salt thereof.

3. A compound according to claim 1 of the formula I in which Ac represents $C_1$–$C_4$-alkoxycarbonyl, X represents oxy, —X—A— represents a radical of the formula —X—alk$_1$—O—Ph—alk$_2$— or —X—alk$_1$—O—Ph—O—alk$_3$— in which alk$_1$, alk$_2$ and alk$_3$ represent identical or different $C_2$–$C_4$-alkylene radicals, and R represents phenyl that is unsubstituted or is mono- or di-substituted by halogen having an atomic number of up to and including 35 or is monosubstituted by trifluoromethyl, nitro or by cyano;

$R_1$ represents phenyl unsubstituted or monosubstituted by $C_1$–$C_4$-alkoxy-$C_2$–$C_4$-alkoxy, $C_1$–$C_4$-alkoxy-$C_1$–$C_4$-alkyl, $C_1$–$C_4$-alkoxy-$C_2$–$C_4$-alkoxy-$C_1$–$C_4$-alkyl, 3- to 5-membered cycloalkyl-$C_1$–$C_4$-alkoxy-$C_2$–$C_4$-alkyl, carbamoyl-$C_1$–$C_4$-alkyl, or by cyano; and $R_2$ and $R_3$ represent $C_1$–$C_4$-alkyl; or an acid addition salt thereof.

4. A compound according to claim 1 of the formula I in which $R_1$ represents a phenyl radical substituted by at least one of halo and lower alkanoyl; pyridyl, 1-oxidized pyridyl, (1,3-dioxa)indanyl, or benzofurazanyl.

5. A compound according to claim 1 of the formula I in which Ac represents $C_1$–$C_4$-alkoxycarbonyl; —X—A— represents a group of the formula —X-alk$_1$—O—Ph—alk$_3$— or —X—alk$_1$—O—Ph—O—alk$_3$—; in which X represents oxy, each of alk$_1$ and alk$_3$, independently of the other, represents $C_2$–$C_4$-alkylene; and Ph represents 1,2-, 1,3- or 1,4-phenylene; and R represents phenyl that is mono- or di-substituted in one or both of the 2- and 3-positions by halogen having an atomic number of up to and including 35 or is monosubstituted by $C_1$–$C_4$-alkoxy in the 3-position, or by nitro in the 2- or 3-position;

$R_1$ represents phenyl monosubstituted by 2-methoxyethyl, 2-isopropoxyethoxymethyl, 2-cyclopropylmethoxyethyl, 2-methoxyethoxy, or by 2-isopropoxyethoxy, in each case in the 4-position, or mono-substituted by cyano in the 2-position; and each of $R_2$ and $R_3$ represents $C_1$–$C_4$-alkyl; or an acid addition salt thereof.

6. A compound according to claim 1 of the formula I in which Ac represents $C_1$–$C_4$-alkoxycarbonyl;

—X—A— represents a group of the formula —X—alk$_1$—O—Ph—alk$_3$— or —X—alk$_1$—O—Ph—O—alk$_3$;

in which X represents oxy;

each of alk$_1$ and alk$_3$ independently of the other, represents $C_2$–$C_4$-alkylene; and Ph represents 1,2-phenylene, 1,3-phenylene, or 1,4-phenylene; and R represents 3-nitrophenyl or 3-methoxy-phenyl;

$R_1$ represents 4-(2-methoxyethyl)-, 4-(2-isopropoxyethoxymethyl)-, 4-(2-cyclopropylmethoxyethyl)-, 4-(2-methoxyethoxy)-4-(2-isopropoxyethoxy)-phenyl or 2-cyanophenyl; and each of $R_2$ and $R_3$ represents $C_1$–$C_4$-alkyl; or an acid addition salt thereof.

7. A compound according to claim 1 of the formula I in which $R_1$ represents phenyl, 2-methyl-, 4-(2-methoxyethyl)-, 4-(2-isopropoxyethoxymethyl)-, 4-(2-methoxyethoxy)-4-(2-isopropoxyethoxy)-, 4-(2-cyclopropylmethoxyethyl)-, 4-carbamoylmethyl-, 2-methoxy-, 2-alkoxy- or 2-cyano-phenyl, 4-indolyl or 2-methyl-4-indolyl, or an acid addition salt thereof.

8. A compound according to claim 1 of the formula I in which Ac represents $C_1$–$C_3$-alkoxycarbonyl, —X—A— represents a group of the formula —X—$C_2H_4$—O—Ph—alk$_3$— or —X—$C_2H_4$—O—Ph—O—alk$_3$— in which X represents oxy, Ph represents 1,4- or 1,2-phenylene, and alk$_3$ represents $C_2$–$C_4$-alkylene, and R represents 3-nitro- or 3-methoxy-phenyl, $R_2$ and $R_3$ represent $C_1$–$C_2$-alkyl, and $R_1$ represents 4-(2-methoxyethyl)-, 4-(2-isopropoxyethoxymethyl)-, 4-(2-cyclopropylmethoxyethyl)- or 4-(2-methoxyethoxy)-phenyl, or $R_1$ represents 2-cyanophenyl, or an acid addition salt thereof.

9. A compound according to claim 1 of the formula I in which Ac represents $C_1$–$C_3$-alkoxycarbonyl, —X—A— represents a group of the formula —X—$C_2H_5$—O—Ph—O—alk$_3$ in which X represents oxy, Ph represents 1,4-phenylene, and alk$_3$ represents ethylene or 1,2-(2-methyl)-propylene, and R represents 3-nitrophenyl, $R_1$ represents 4-(2-methoxyethyl)- or 4-(2-isopropoxyethoxymethyl)-phenyl, and $R_2$ and $R_3$ represent $C_1$–$C_2$-alkyl, or an acid addition salt thereof.

10. 1,4-dihydro-2,6-dimethyl-4-(m-nitrophenyl)-pyridine-3,5-dicarboxylic acid 3-{{{2-{{p-{2-[[3-[4-(2-isopropoxyethoxymethyl)-phenoxy]-2-hydroxy-propylamino]]-ethoxy}-phenoxy}}-ethyl}}} ester 5-methyl ester or an acid addition salt thereof, according to claim 1.

11. A compound of claim 1 which is 1,4-dihydro-2,6-dimethyl-4-(m-nitrophenyl)-pyridine-3,5-dicarboxylic acid 3-{{{2-{{p-{2-[3-(o-cyanophenoxy)-2-hydroxypropylamino]-ethyl}-phenoxy}}-ethyl}}} ester 5-methyl ester, or an acid addition salt thereof.

12. A compound of claim 1 which is 1,4-dihydro-2,6-dimethyl-4-(m-nitrophenyl)-pyridine-3,5-dicarboxylic acid 3-{{{2-{{p-{2-[3-(o-cyanophenoxy)-2-hydroxypropylamino]-ethoxy}-phenoxy}}-ethyl}}} ester 5-methyl ester, or an acid addition salt thereof.

13. A compound of claim 1 which is 1,4-dihydro-2,6-dimethyl-4-(m-nitrophenyl)-pyridine-3,5-dicarboxylic acid 3-{{{2-{{p-{2-[3-(o-cyanophenoxy)-2-hydroxypropylamino]-2-methylpropoxy}-phenoxy}}-ethyl}}} ester 5-methyl ester, or an acid addition salt thereof.

14. A compound of claim 1 which is 1,4-dihydro-2,6-dimethyl-4-(m-nitrophenyl)-pyridine-3,5-dicarboxylic acid 3-{{{2-{{p-{2-[[3-[p-(2-methoxyethoxy)-phenoxy]-2-hydroxypropylamino]]-2-methylpropoxy}-phenoxy}}-ethyl}}} ester 5-methyl ester, or an acid addition salt thereof.

15. A compound of claim 1 which is 1,4-dihydro-2,6-dimethyl-4-(m-nitrophenyl)-pyridine-3,5-dicarboxylic acid 3-{{{2-{{p-{2-[[3-[4-(2-isopropoxyethoxymethyl)-phenoxy]-2-hydroxypropylamino]]-2-methylpropoxy}-phenoxy}}-ethyl}}} ester 5-methyl ester, or an acid addition salt thereof.

16. A compound of claim 1 which is 1,4-dihydro-2,6-dimethyl-4-(m-nitrophenyl)-pyridine-3,5-dicarboxylic acid 3-{{{2-{{p-{2-[[3-[4-(2-methoxyethyl)-phenoxy]-2-hydroxypropylamino]]-ethoxy}-phenoxy}}-ethyl}}} ester 5-methyl ester or an acid addition salt thereof.

17. A compound of claim 1 which is 1,4-dihydro-2,6-dimethyl-4-(m-nitrophenyl)-pyridine-3,5-dicarboxylic acid 3-{{{2-{{p-{2-[[3-[4-(2-methoxyethoxy)-phenoxy]-2-hydroxypropylamino]]-ethoxy}-phenoxy}}-ethyl}}} ester 5-methyl ester, or an acid addition salt thereof.

18. A compound of claim 1 which is 1,4-dihydro-2,6-dimethyl-4-(m-nitrophenyl)-pyridine-3,5-dicarboxylic acid 3-{{{2-{{p-{2-[[3-[4-(2-cyclopropylmethoxyethyl)-phenoxy]-2-hydroxypropylamino]]-ethoxy}-phenoxy}}-ethyl}}} ester 5-methyl ester, or an acid addition salt thereof.

19. A compound of claim 1 which is 1,4-dihydro-2,6-dimethyl-4-(m-nitrophenyl)-pyridine-3,5-dicarboxylic acid 3-{{{2-{{p-{2-[[3-[4-(2-isopropoxyethoxy)-phenoxy]-2-hydroxypropylamino]]-ethoxy}-phenoxy}}-ethyl}}} ester 5-methyl ester, or an acid addition salt thereof.

20. A compound of claim 1 which is 1,4-dihydro-2,6-dimethyl-4-(m-nitrophenyl)-pyridine-3,5-dicarboxylic acid 3-{{{2-{{o-{2-[[3-[4-[2-isopropoxyethoxymethyl)-phenoxy]-2-hydroxypropylamino]]-ethoxy}-phenoxy}}-ethyl}}} ester 5-methyl ester, or an acid addition salt thereof.

21. A compound of claim 1 which is 1,4-dihydro-2,6-dimethyl-4-(m-nitrophenyl)-pyridine-3,5-dicarboxylic acid 3-{{{2-{{p-{2-[[3-[4-(2-isopropoxyethoxymethyl)-phenoxy]-2-hydroxypropylamino]]-ethoxy}-phenoxy}}-ethyl}}} ester 5-methyl ester, or an acid addition salt thereof.

22. An antihypertensive, antianginal and anti-arrhythmic pharmaceutical composition comprising a pharmaceutically effective amount of a compound according to claim 1 or a pharmaceutically acceptable salt thereof in addition to a pharmaceutically acceptable carrier.

23. A method for the treatment of hypertension, Angina perctoris and arrhythmia in human or animal body comprising administering a pharmaceutically effective amount of a compound according to claim 1 or a pharmaceutically acceptable salt thereof.

* * * * *